United States Patent
Biedermann

(10) Patent No.: US 9,918,758 B2
(45) Date of Patent: Mar. 20, 2018

(54) MODULAR BONE PLATE AND CONNECTOR PIECE FOR A MODULAR BONE PLATE

(75) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 694 days.

(21) Appl. No.: 14/123,070

(22) PCT Filed: Jun. 15, 2012

(86) PCT No.: PCT/IB2012/053035
§ 371 (c)(1),
(2), (4) Date: Nov. 27, 2013

(87) PCT Pub. No.: WO2012/172517
PCT Pub. Date: Dec. 20, 2012

(65) Prior Publication Data
US 2014/0100572 A1    Apr. 10, 2014

Related U.S. Application Data

(60) Provisional application No. 61/497,972, filed on Jun. 17, 2011.

(51) Int. Cl.
*A61B 17/80* (2006.01)
*A61B 17/70* (2006.01)

(52) U.S. Cl.
CPC ...... *A61B 17/8023* (2013.01); *A61B 17/7059* (2013.01); *A61B 17/80* (2013.01); *A61B 17/8042* (2013.01); *A61B 17/8061* (2013.01)

(58) Field of Classification Search
CPC ..... A61B 17/58; A61B 17/7059; A61B 17/80; A61B 17/8023; A61B 17/8033;
(Continued)

(56) References Cited

U.S. PATENT DOCUMENTS 5,484,439 A    1/1996   Olson et al.
5,520,690 A *  5/1996   Errico ............... A61B 17/7037
                                                    606/287

(Continued)

FOREIGN PATENT DOCUMENTS

CN    101175449 A    5/2008
CN    101557767 A    10/2009
(Continued)

OTHER PUBLICATIONS

Hoffmeier, Konrad, Machine Translation of the Description of DE 102009055826 A1.*

(Continued)

*Primary Examiner* — Matthew Lawson
*Assistant Examiner* — Amy Sipp
(74) *Attorney, Agent, or Firm* — Gordon & Jacobson, P.C.

(57) ABSTRACT

A modular bone plate is provided including at least a first and a second member each having a top surface and a bottom surface, the first member comprising a male connection portion with a single hole extending from the top surface to the bottom surface and the second member comprising a female connection portion with a single hole extending from the top surface to the bottom surface, wherein the male connection portion is insertable into the female connection portion such that the holes overlap and wherein an anchor or a plug member is insertable into the holes when they overlap.

13 Claims, 42 Drawing Sheets

FEMALE / MALE CONNECTOR PIECE

(58) Field of Classification Search
CPC ............ A61B 17/8042; A61B 17/8047; A61B 17/8052; A61B 17/8057; A61B 17/8061
See application file for complete search history.

(56) References Cited

U.S. PATENT DOCUMENTS

| | | |
|---|---|---|
| 2004/0074189 A1 | 4/2004 | Deschenes |
| 2004/0102778 A1 | 5/2004 | Huebner et al. |
| 2006/0100625 A1 | 5/2006 | Ralph et al. |
| 2006/0229610 A1 | 10/2006 | Piehl |
| 2006/0276794 A1* | 12/2006 | Stern .................. A61B 17/7059 606/71 |
| 2007/0276383 A1* | 11/2007 | Rayhack ................ A61B 17/15 606/86 B |
| 2008/0039847 A1* | 2/2008 | Piper .................. A61B 17/7059 606/279 |
| 2009/0036930 A1* | 2/2009 | Allison .............. A61B 17/8019 606/280 |
| 2009/0082813 A1* | 3/2009 | Long ...................... A61B 17/80 606/282 |
| 2010/0121328 A1 | 5/2010 | Reitzig et al. |
| 2010/0274248 A1* | 10/2010 | Overes ................ A61B 17/7059 606/71 |
| 2012/0029579 A1 | 2/2012 | Bottlang et al. |
| 2014/0081269 A1 | 3/2014 | Biedermann |

FOREIGN PATENT DOCUMENTS

| | | | |
|---|---|---|---|
| DE | 102009055826 | * 5/2011 | ......... A61B 17/8047 |
| JP | 2006-507898 A | 3/2006 | |
| WO | WO 2004/049903 A2 | 6/2004 | |
| WO | WO 2006/102081 A1 | 9/2006 | |
| WO | WO 2008/057861 A2 | 5/2008 | |
| WO | WO 2009/105066 A1 | 8/2009 | |
| WO | WO 2012/172519 A1 | 12/2012 | |

OTHER PUBLICATIONS

International Preliminary Report on Patentability and Written Opinion for International Application No. PCT/IB2012/053035, dated Dec. 17, 2013, 6 sheets.

International Search Report and Written Opinion of corresponding to PCT/IB2012/053035, dated Oct. 1, 2012, 9 pages.

International Search Report and Written Opinion corresponding to PCT/IB2012/053037, dated Sep. 13, 2012, 8 pages.

International Preliminary Report on Patentability and Written Opinion for International Application No. PCT/IB2012/053037, dated Dec. 17, 2013, 6 sheets.

Office action for U.S. Appl. No. 14/123,078, dated May 31, 2016, 14 sheets.

Final Office action for U.S. Appl. No. 14/123,078, dated Dec. 21, 2016, 15 sheets.

Office action for U.S. Appl. No. 14/123,078, dated Jun. 1, 2017, 29 sheets.

* cited by examiner

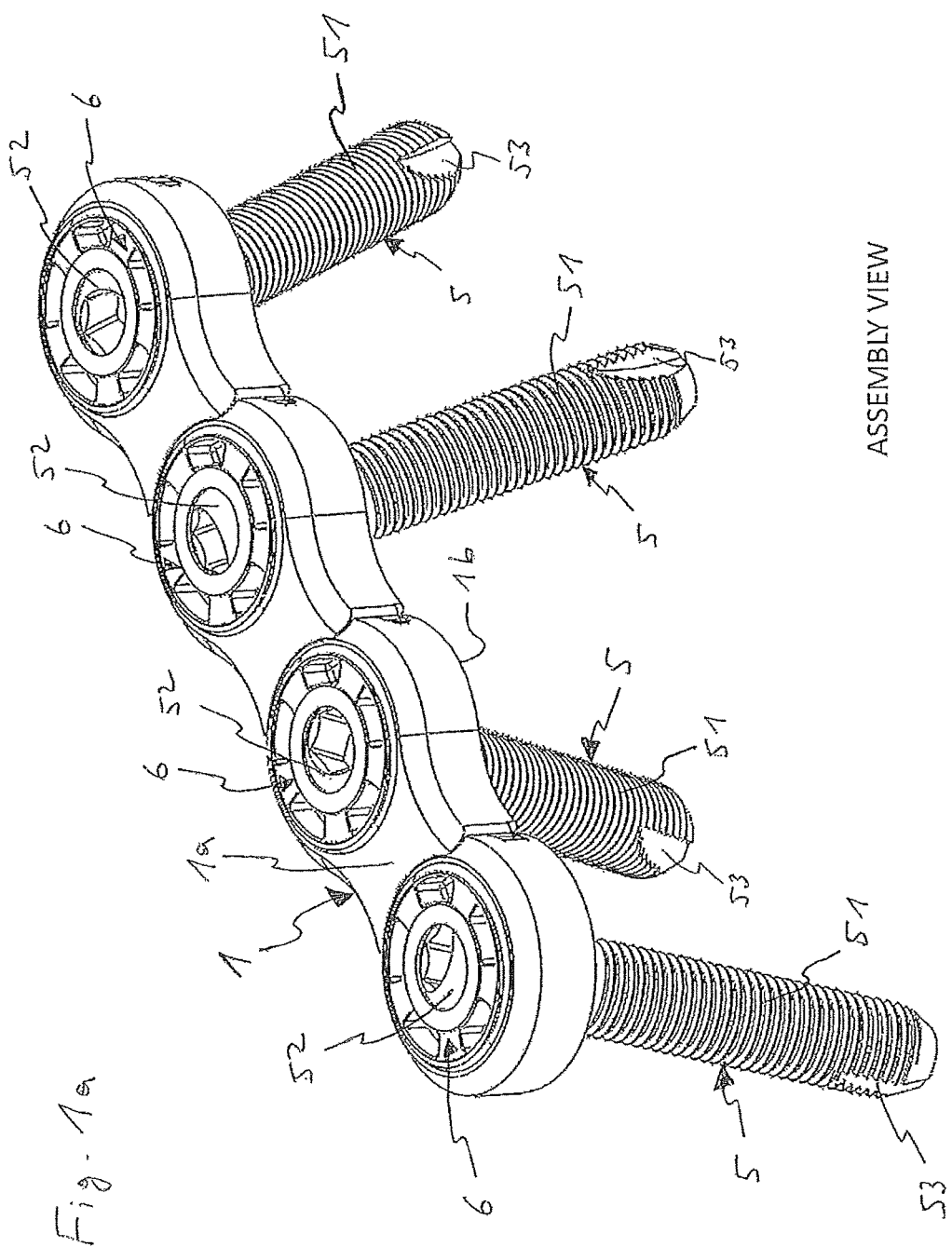

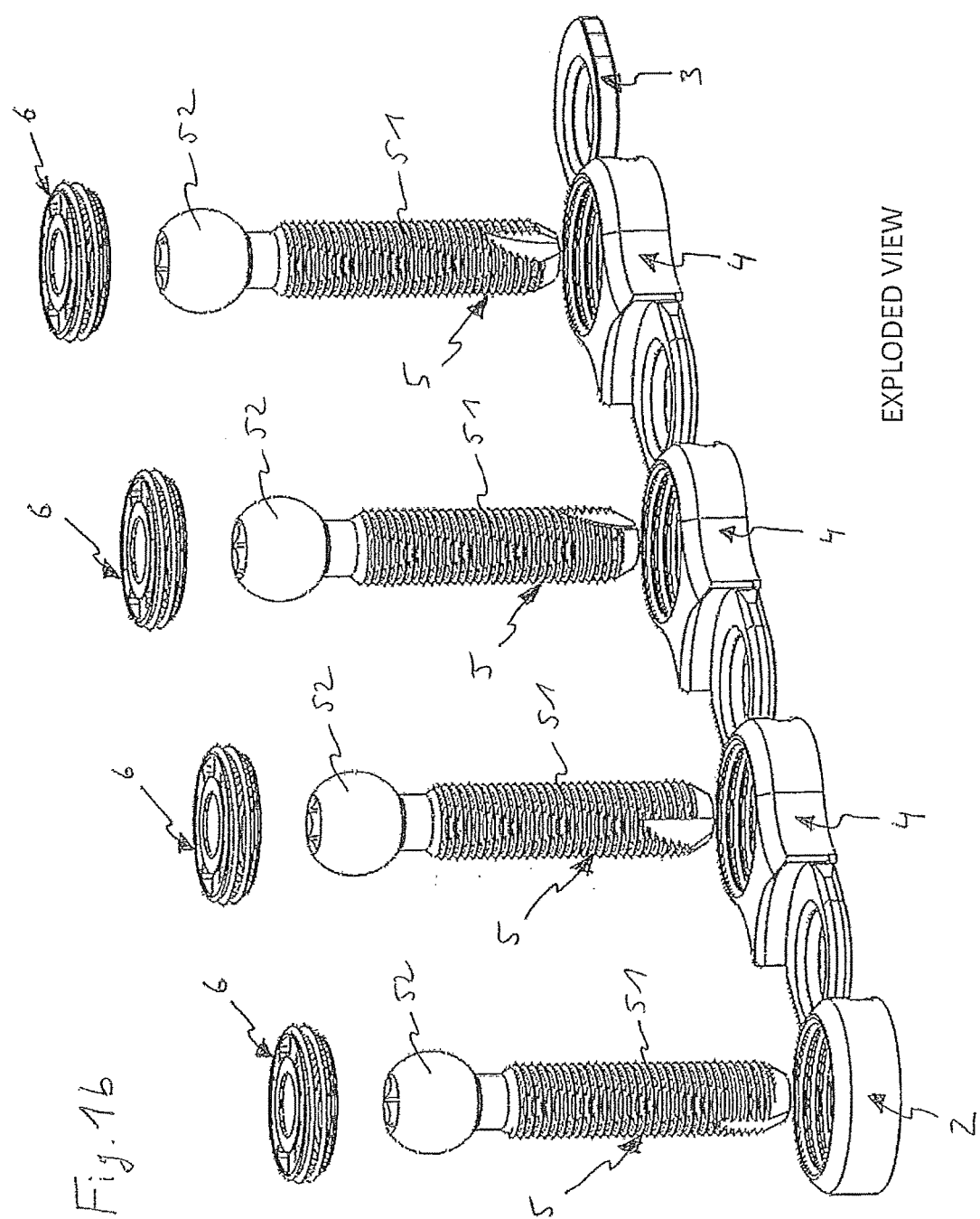

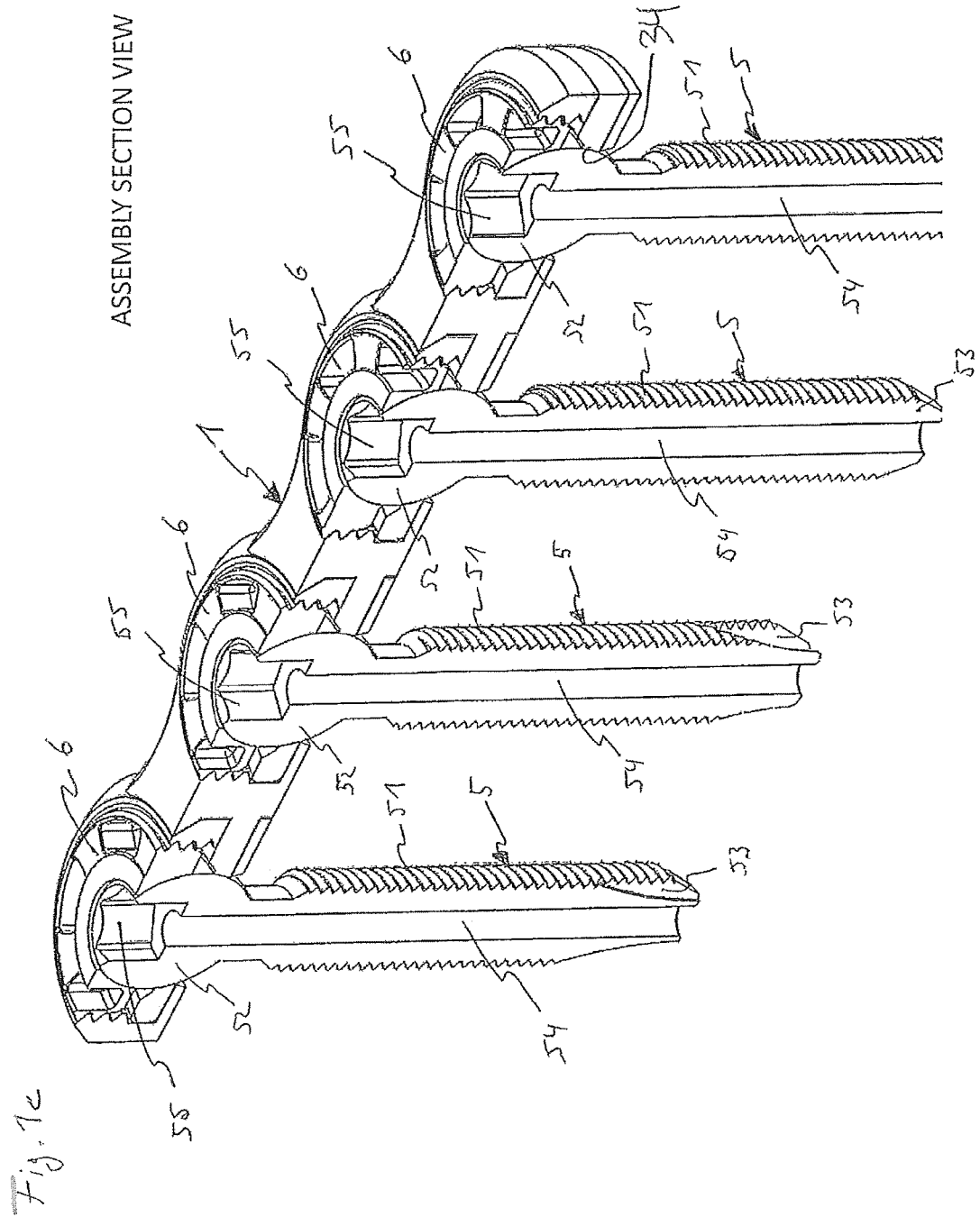

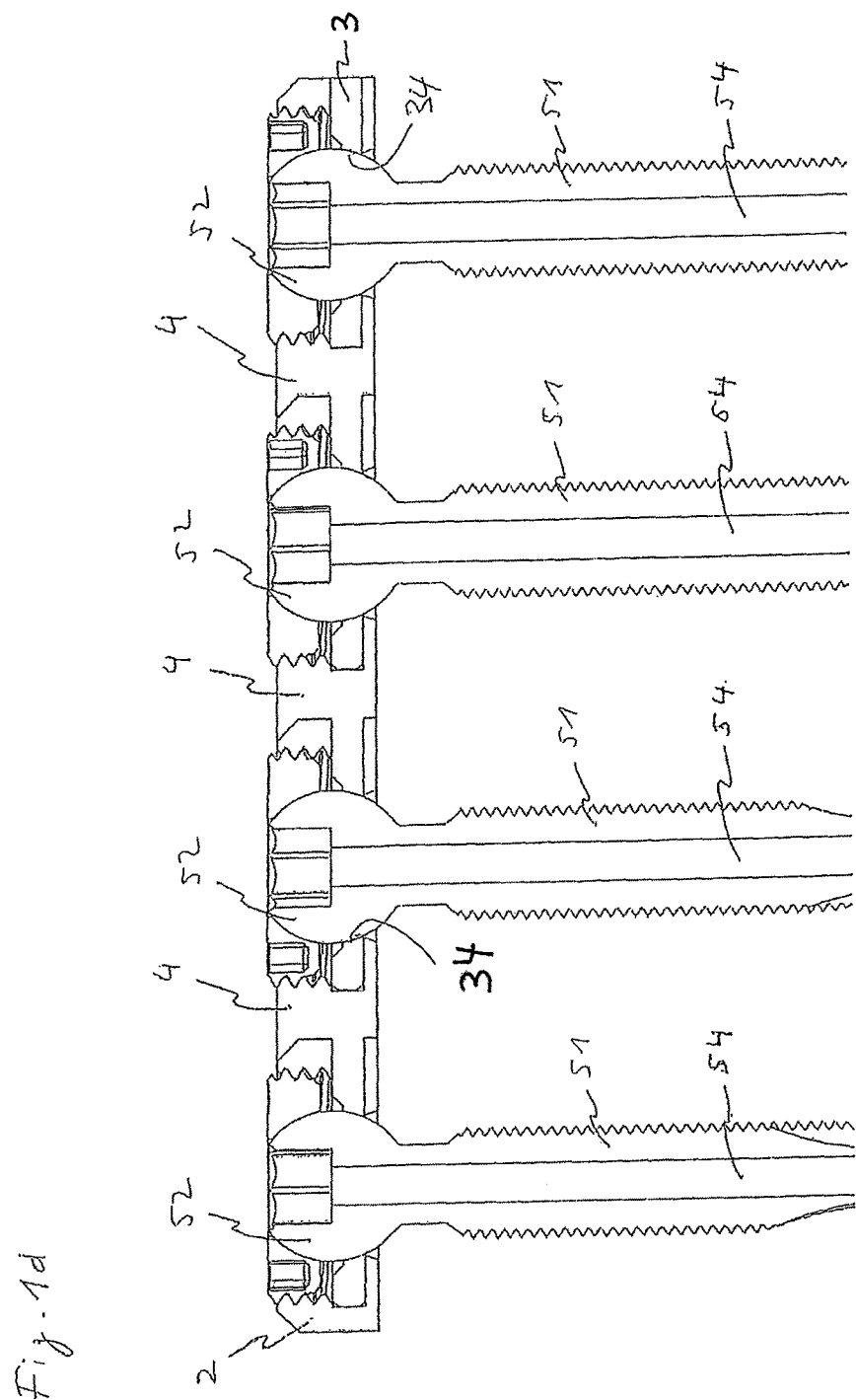

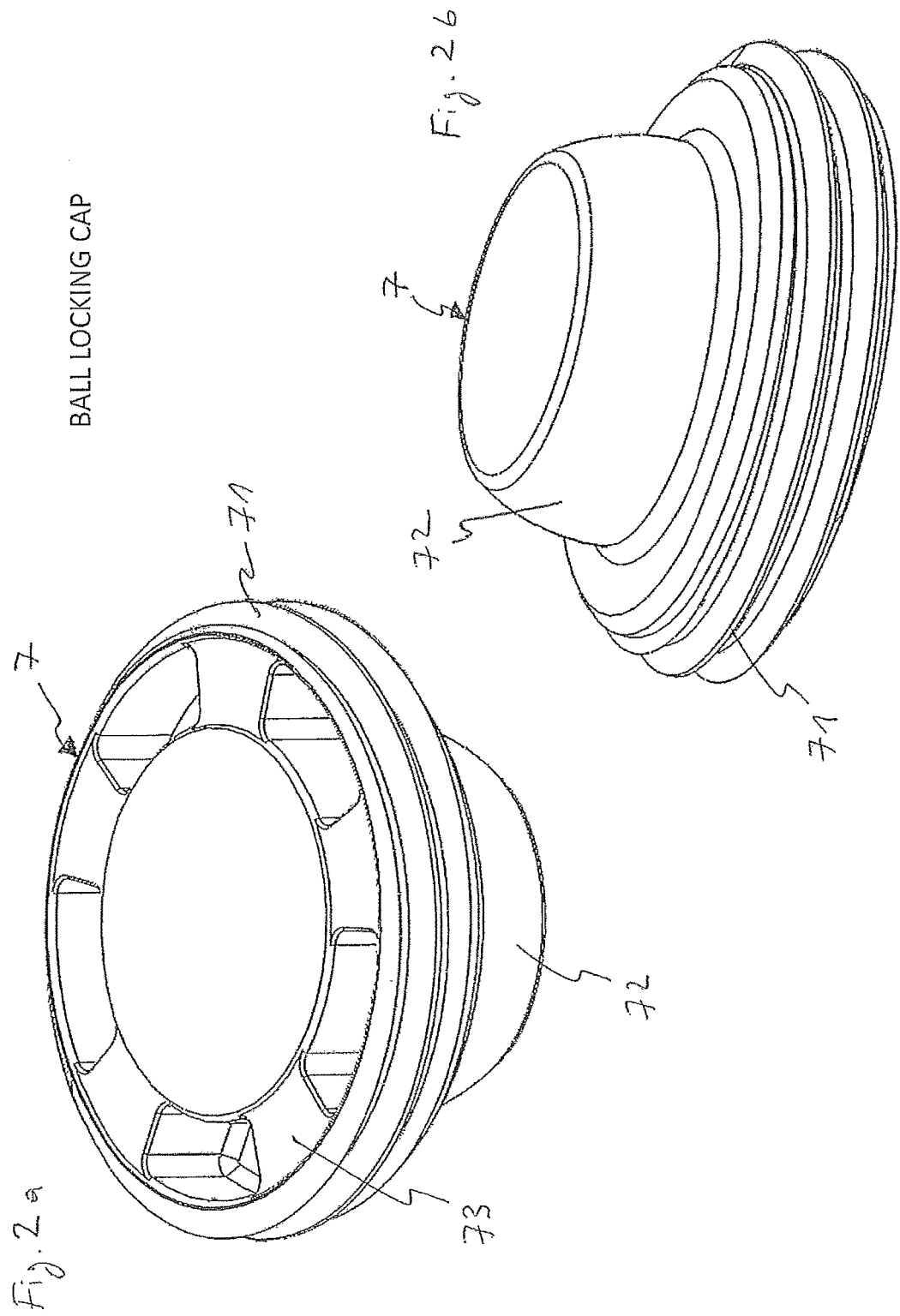

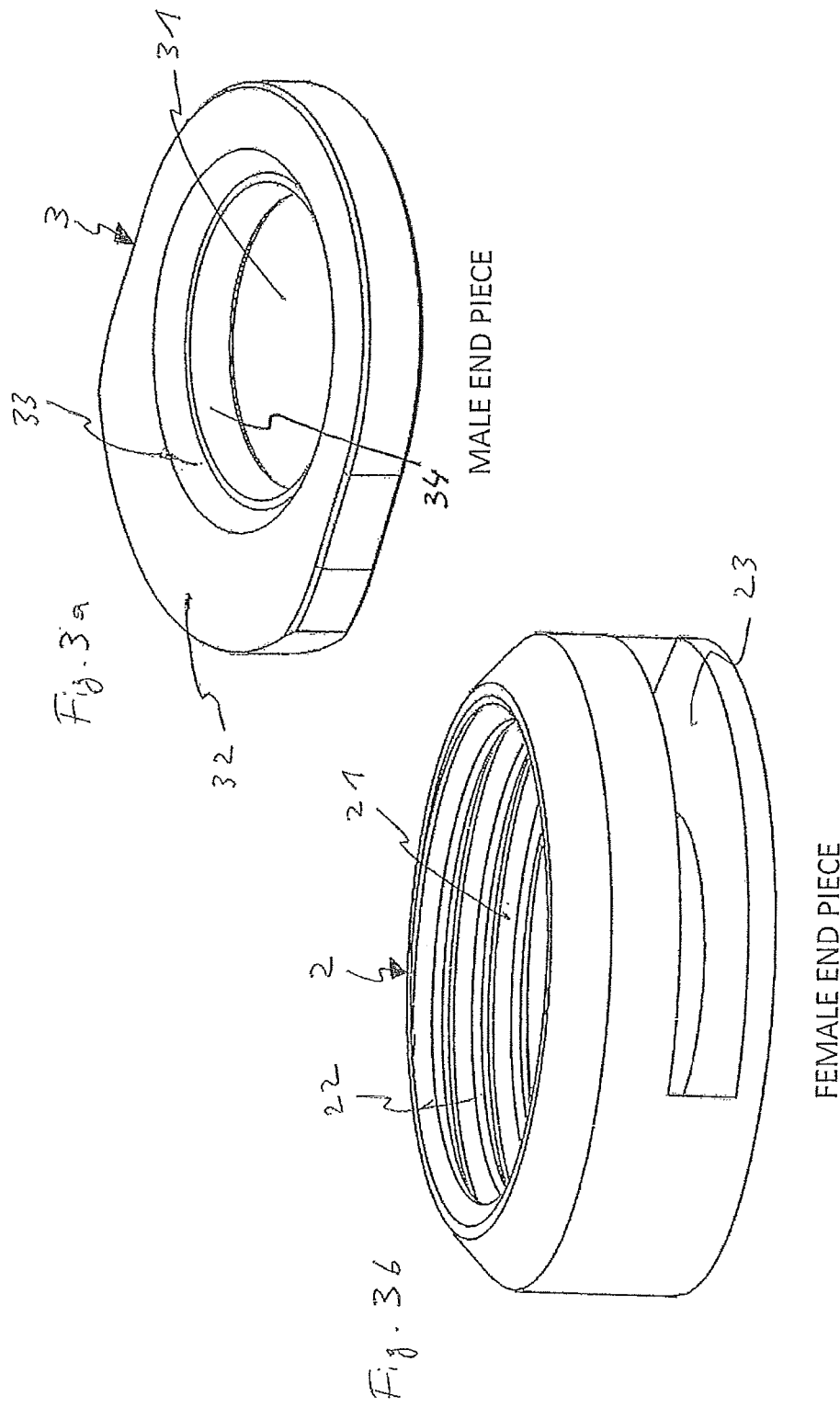

FEMALE / MALE CONNECTOR PIECE

ANGLED CONFIGURATION

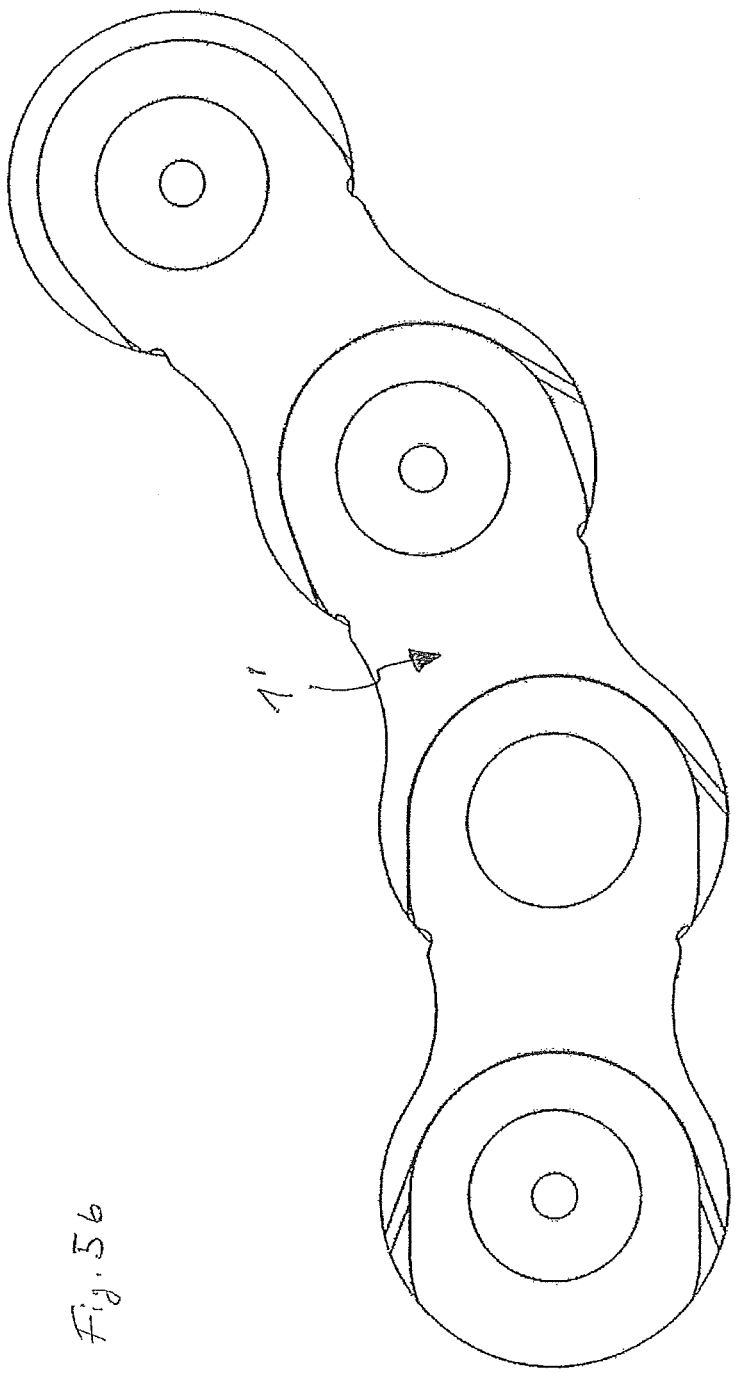

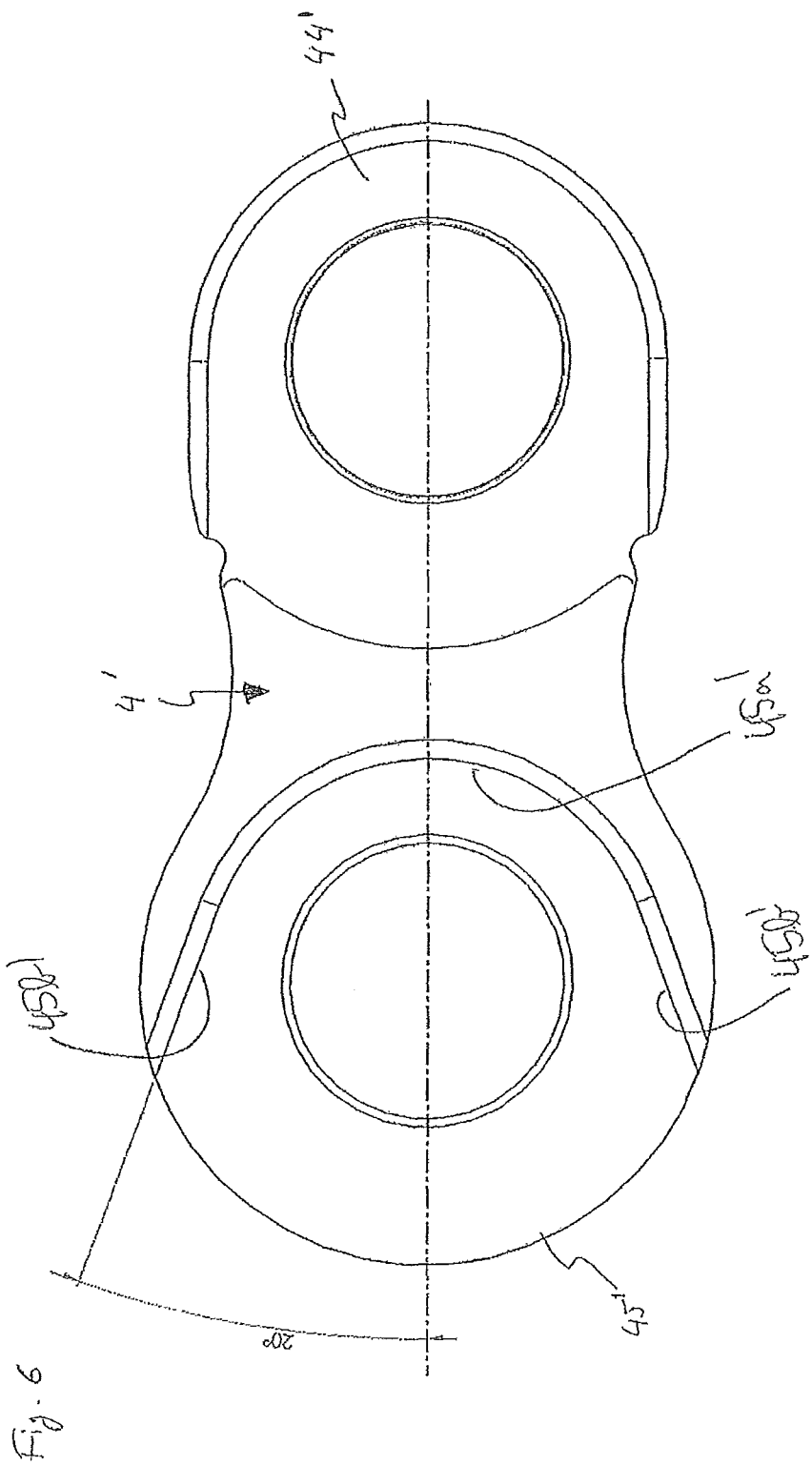

4.5 to 3.5 to 2.5 ASSEMBLY FRONT VIEW

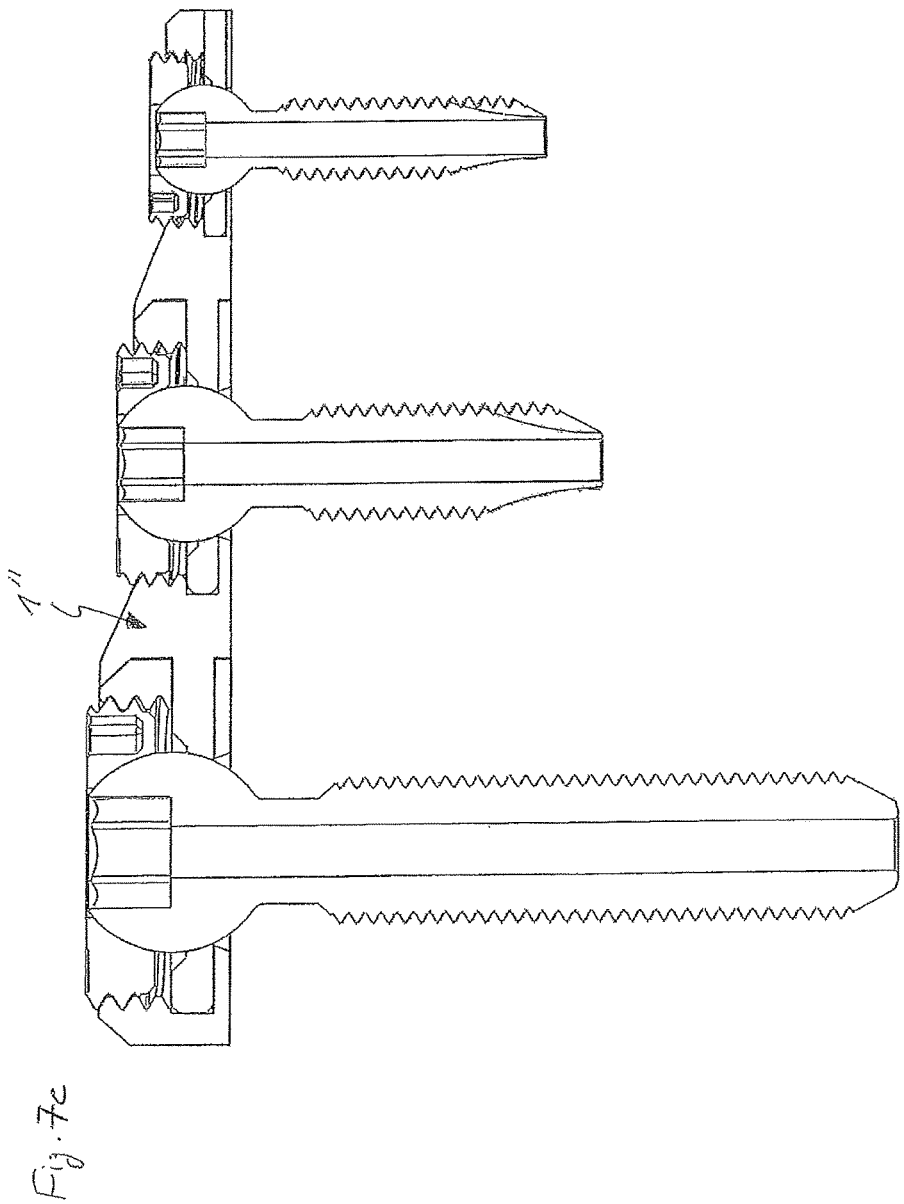

4.5 to 3.5 to 2.5 SECTION ISO VIEW

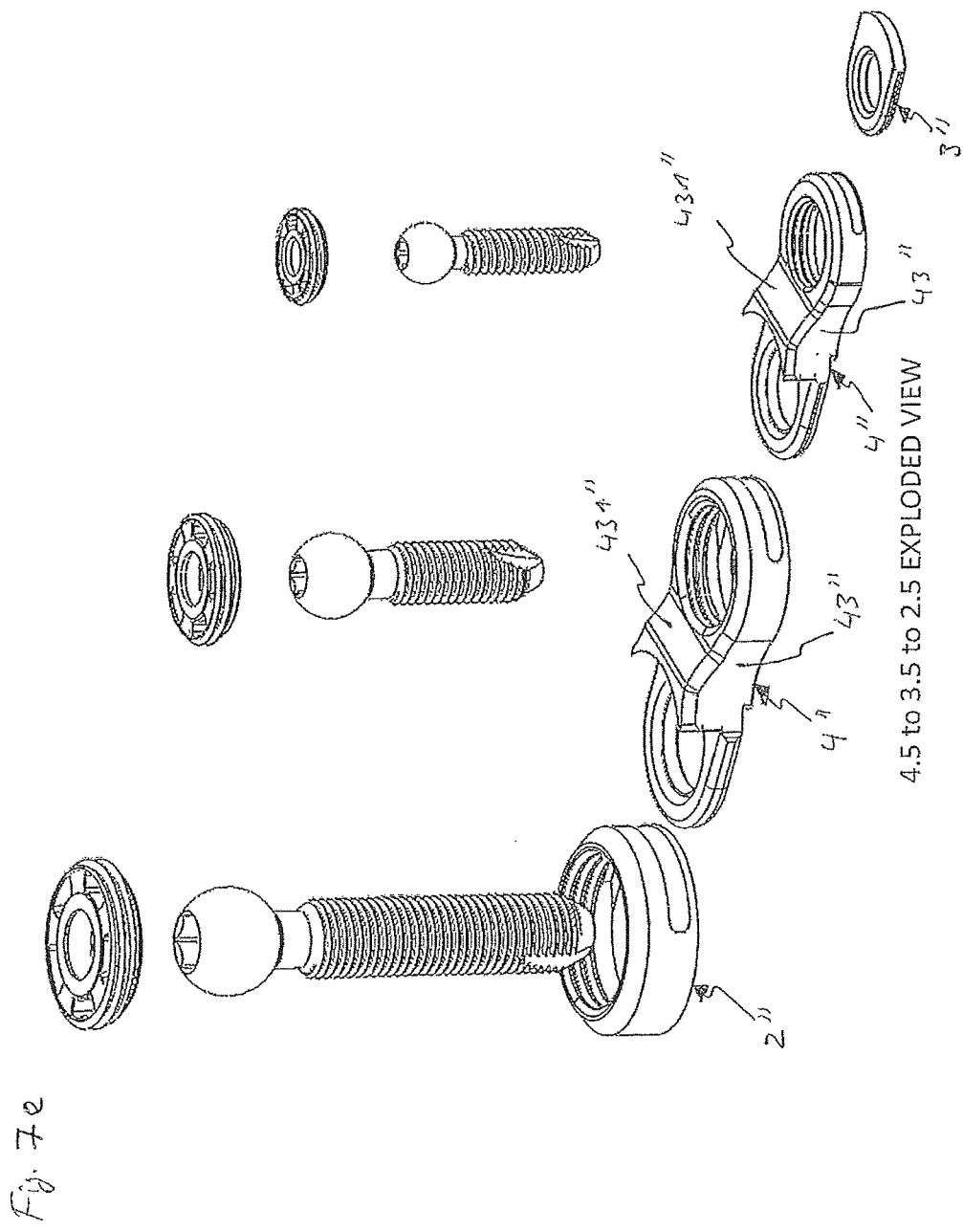

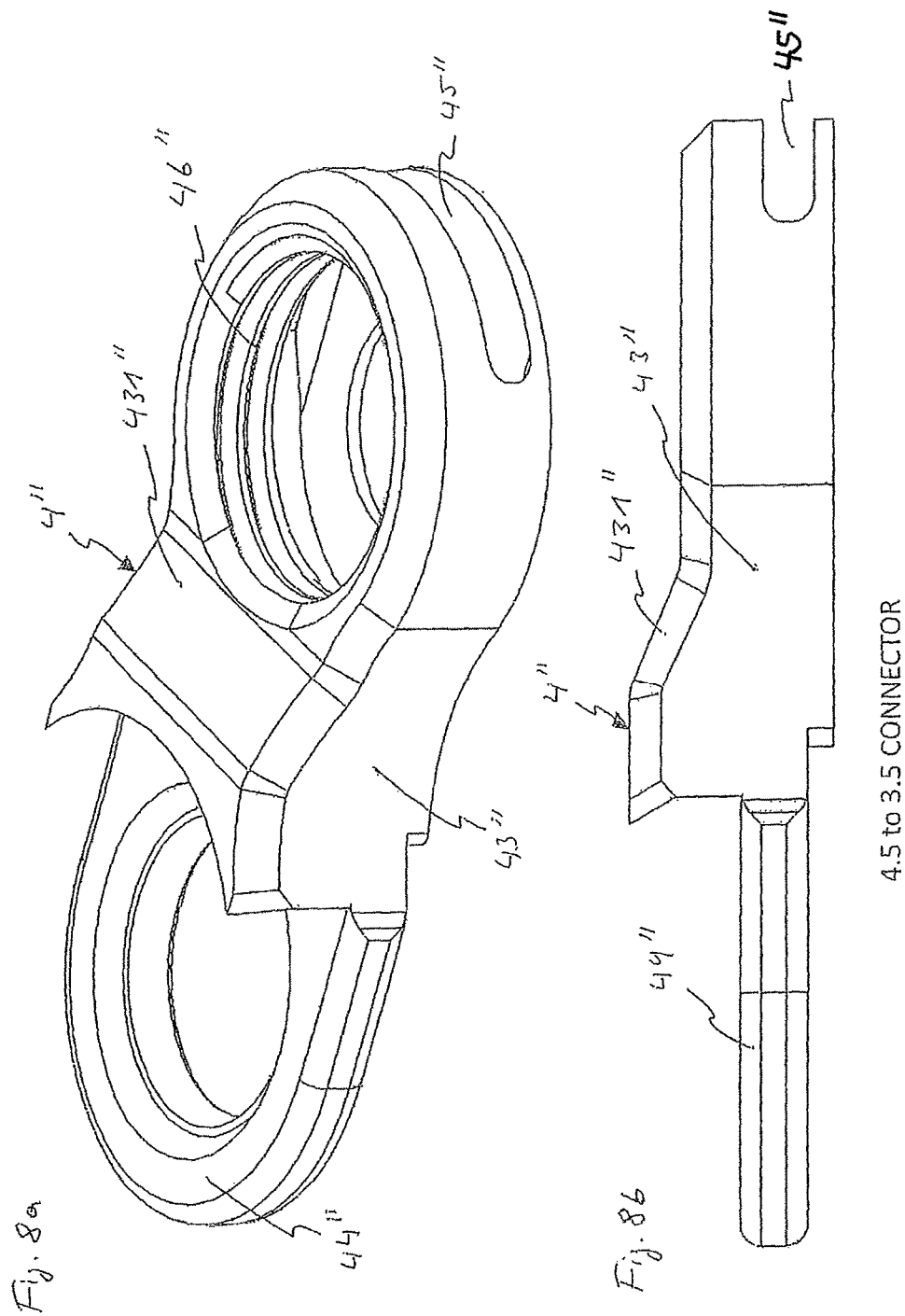

3.5 to 2.5 CONNECTOR

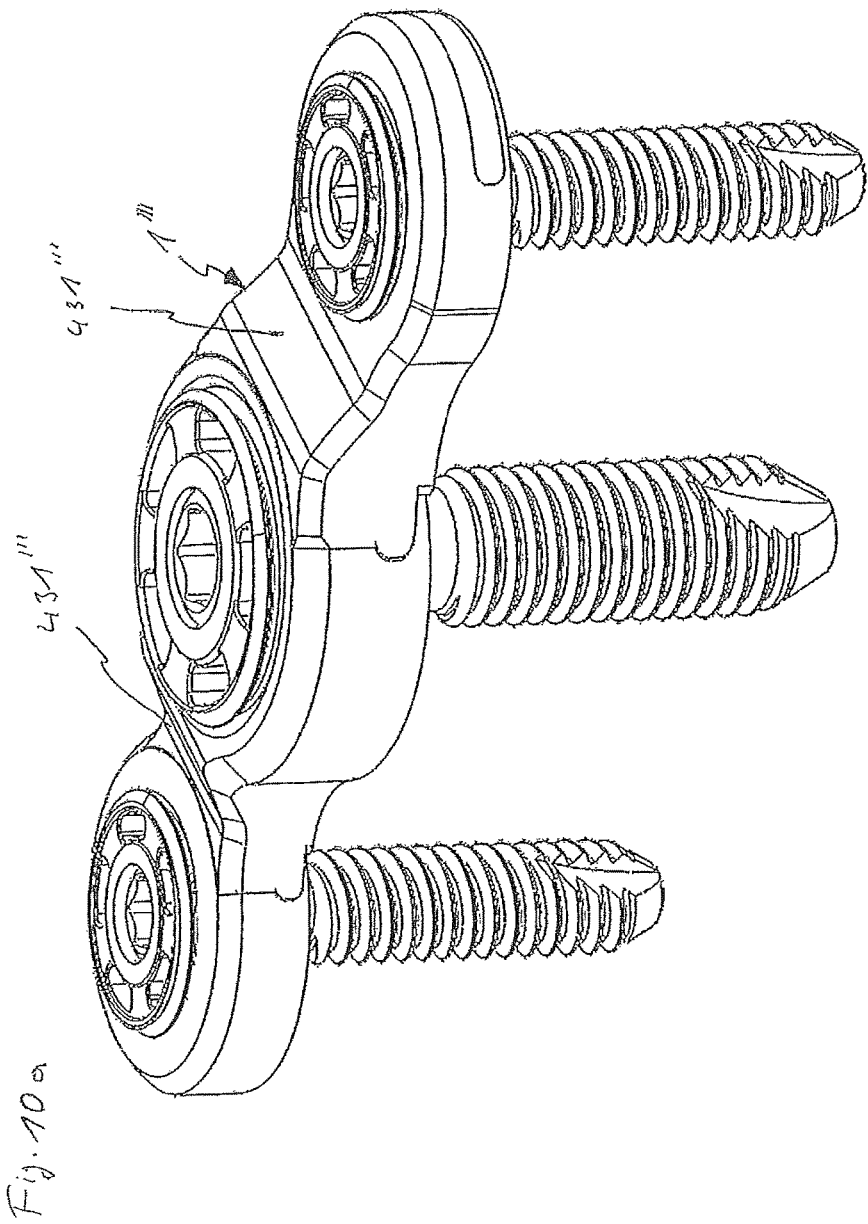

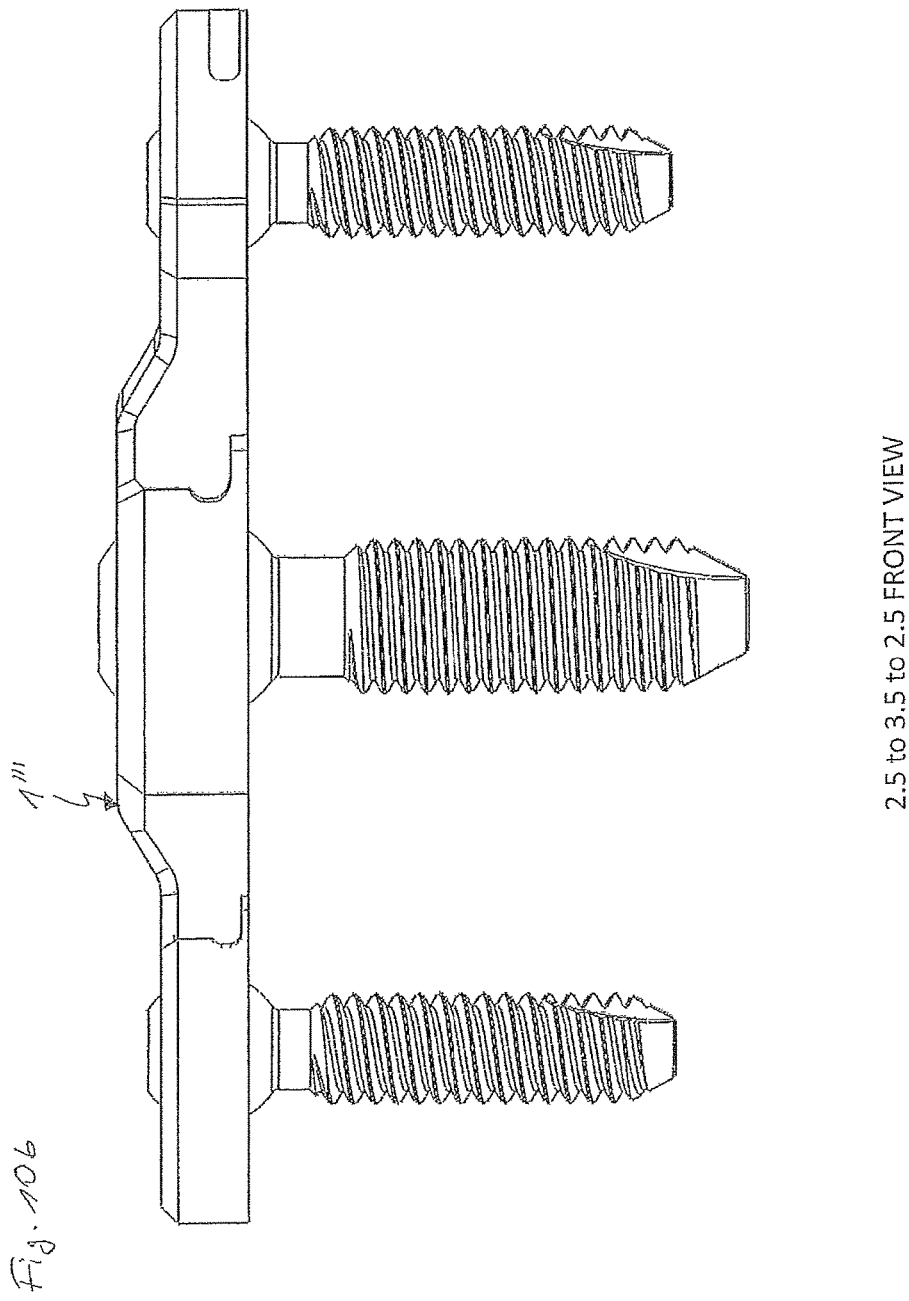

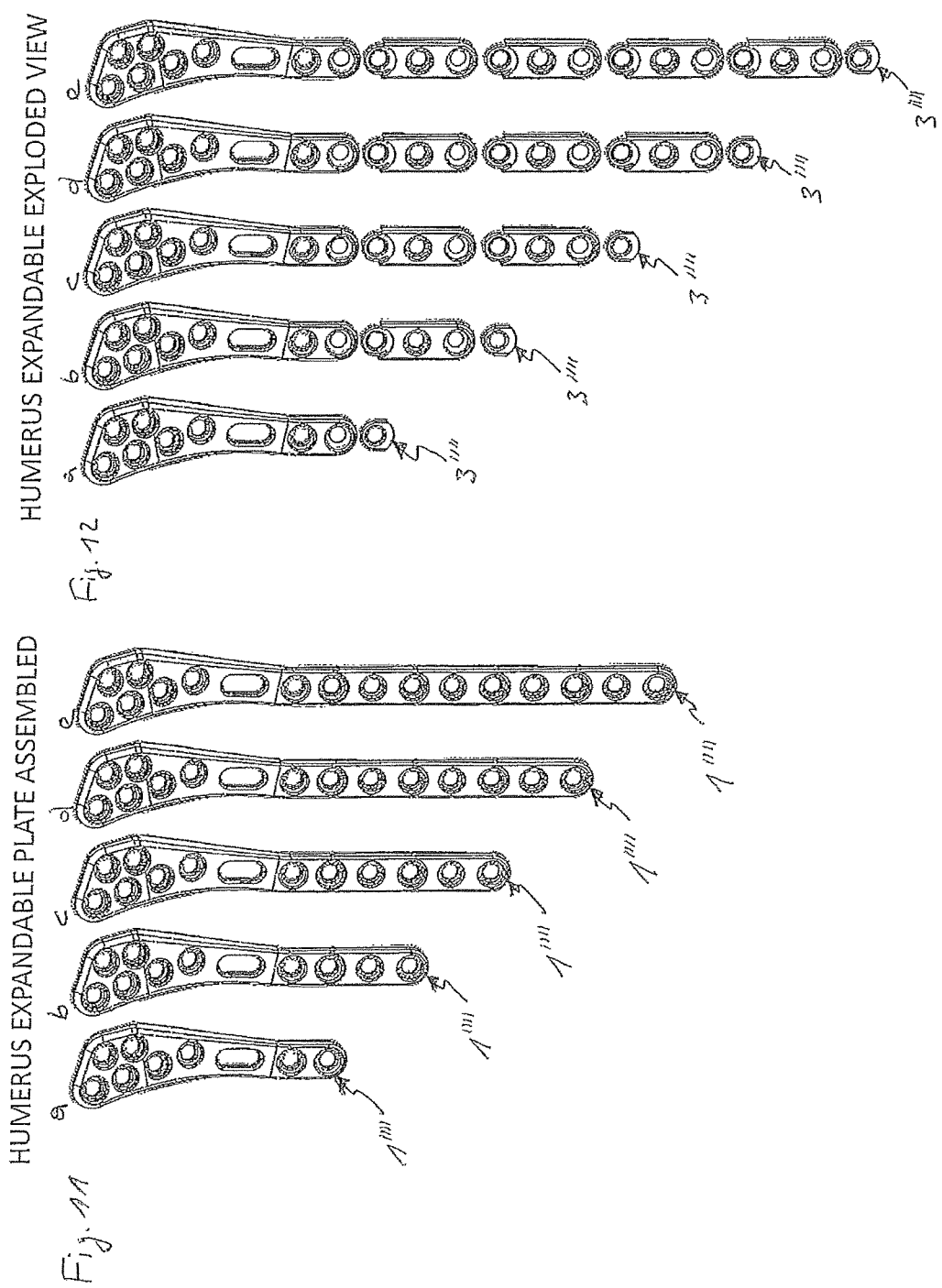

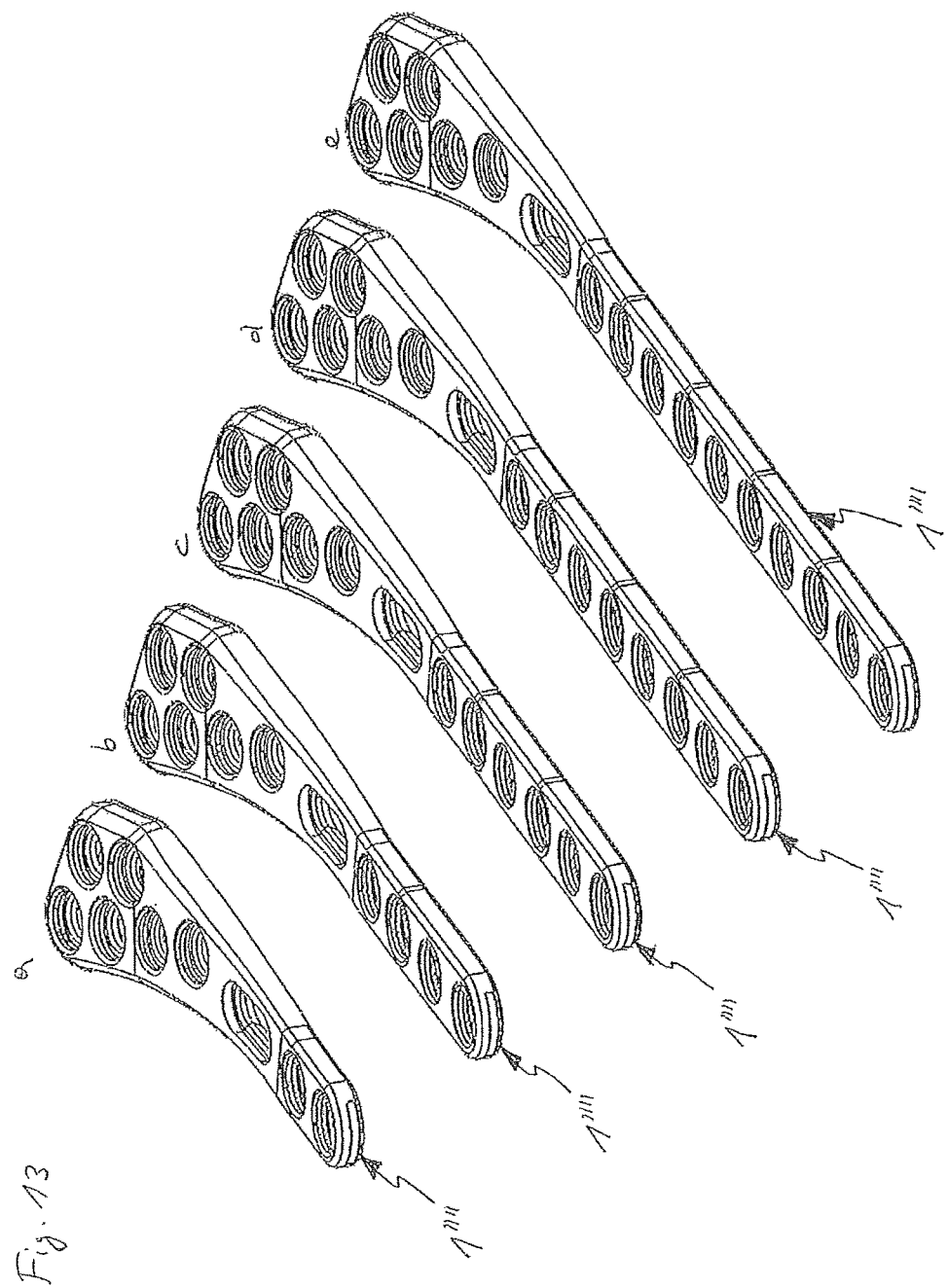

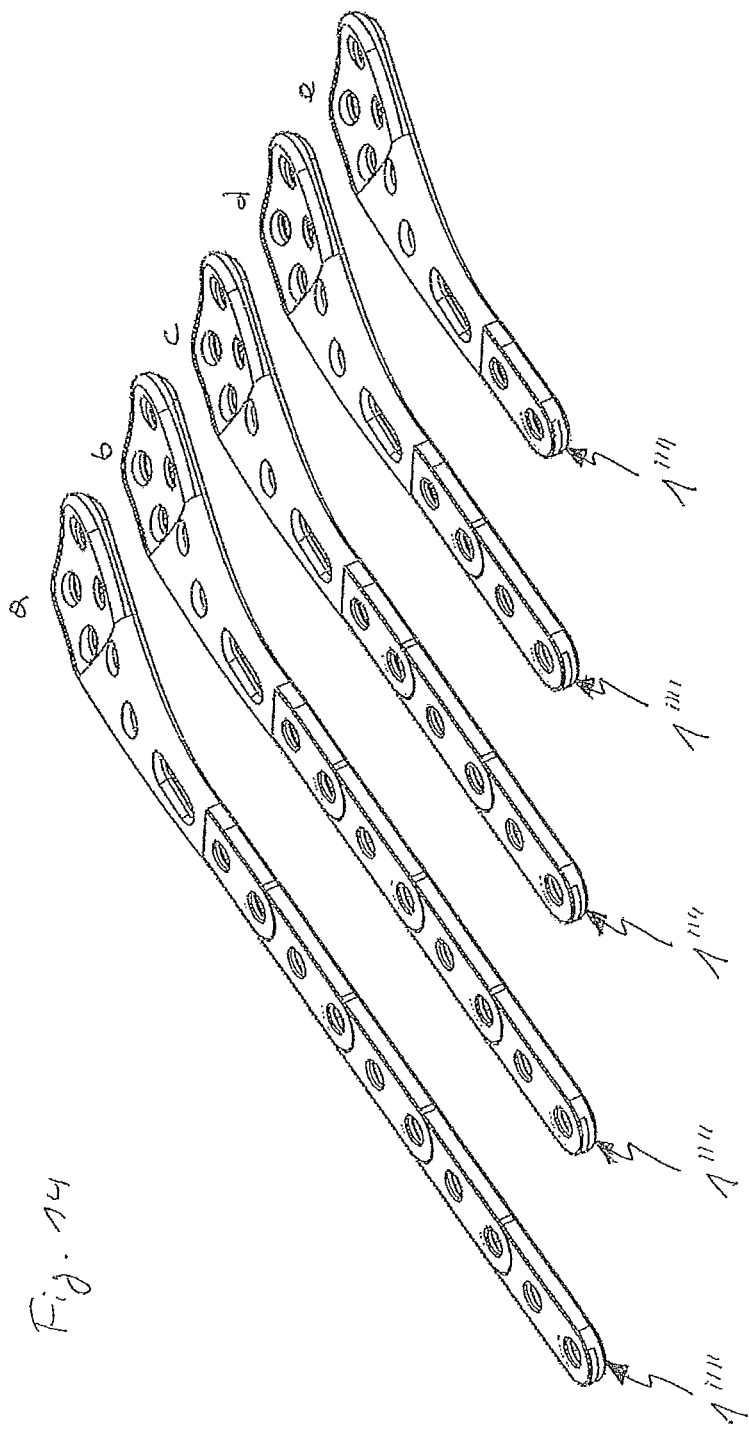

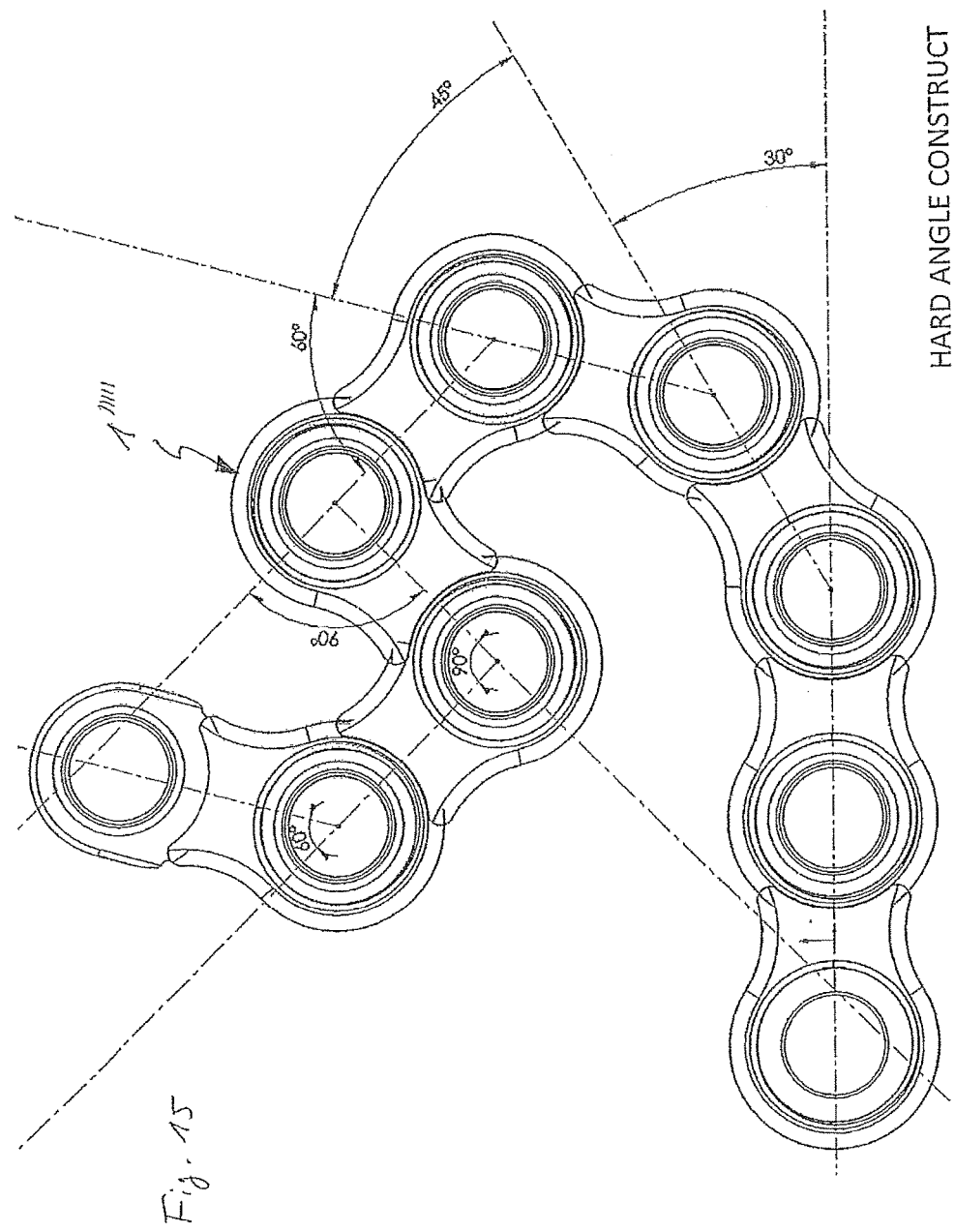

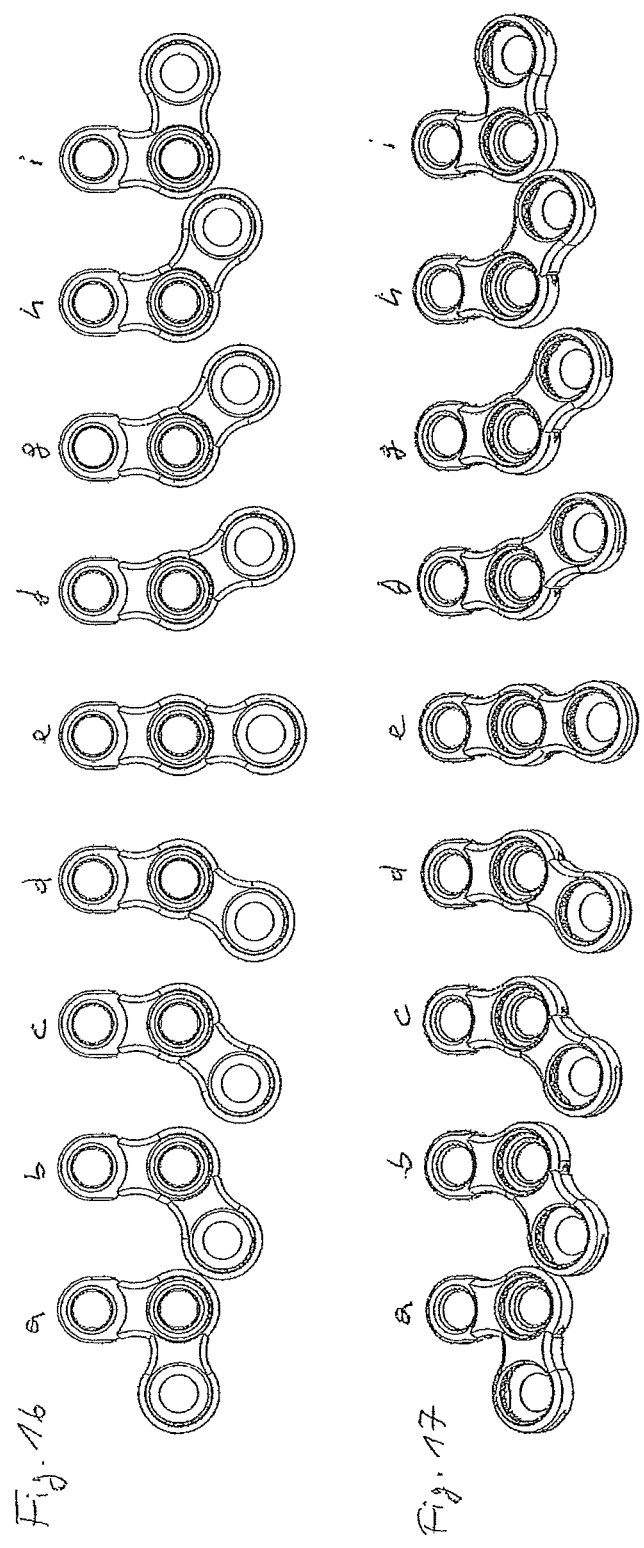

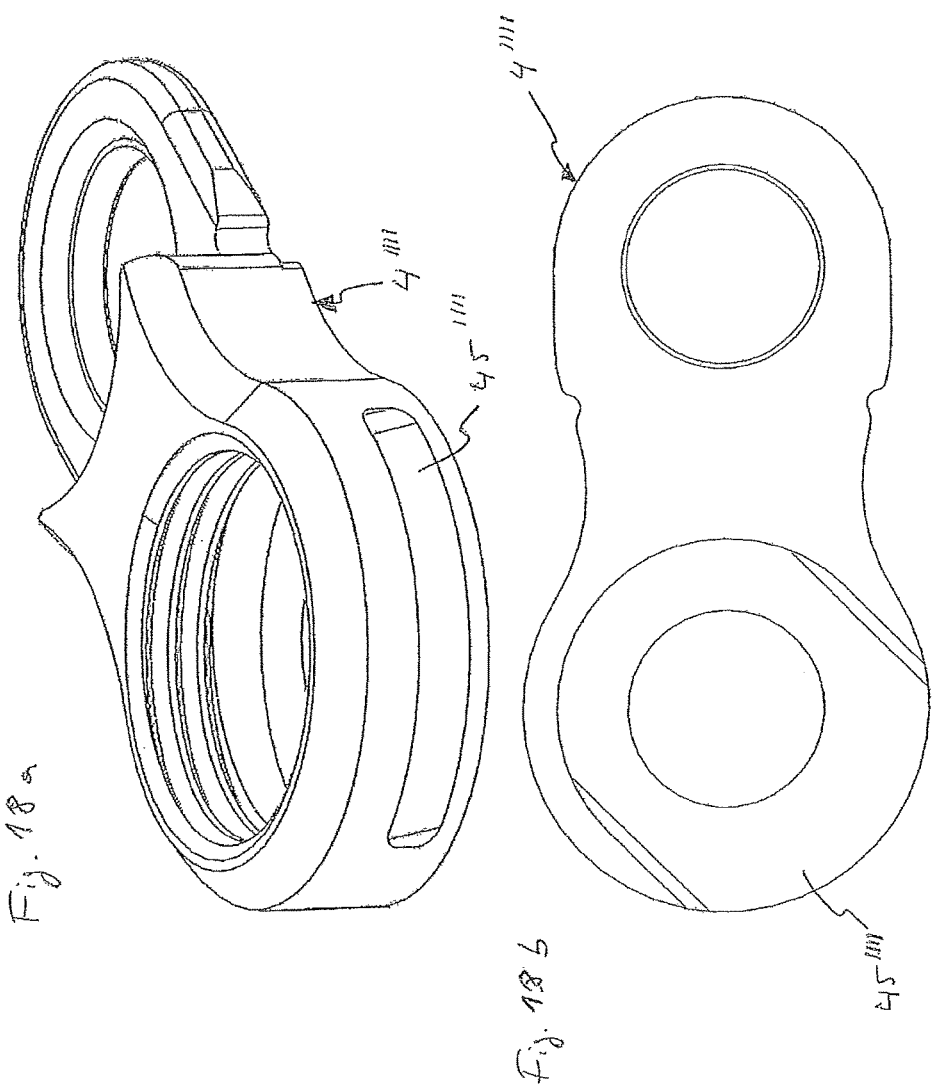

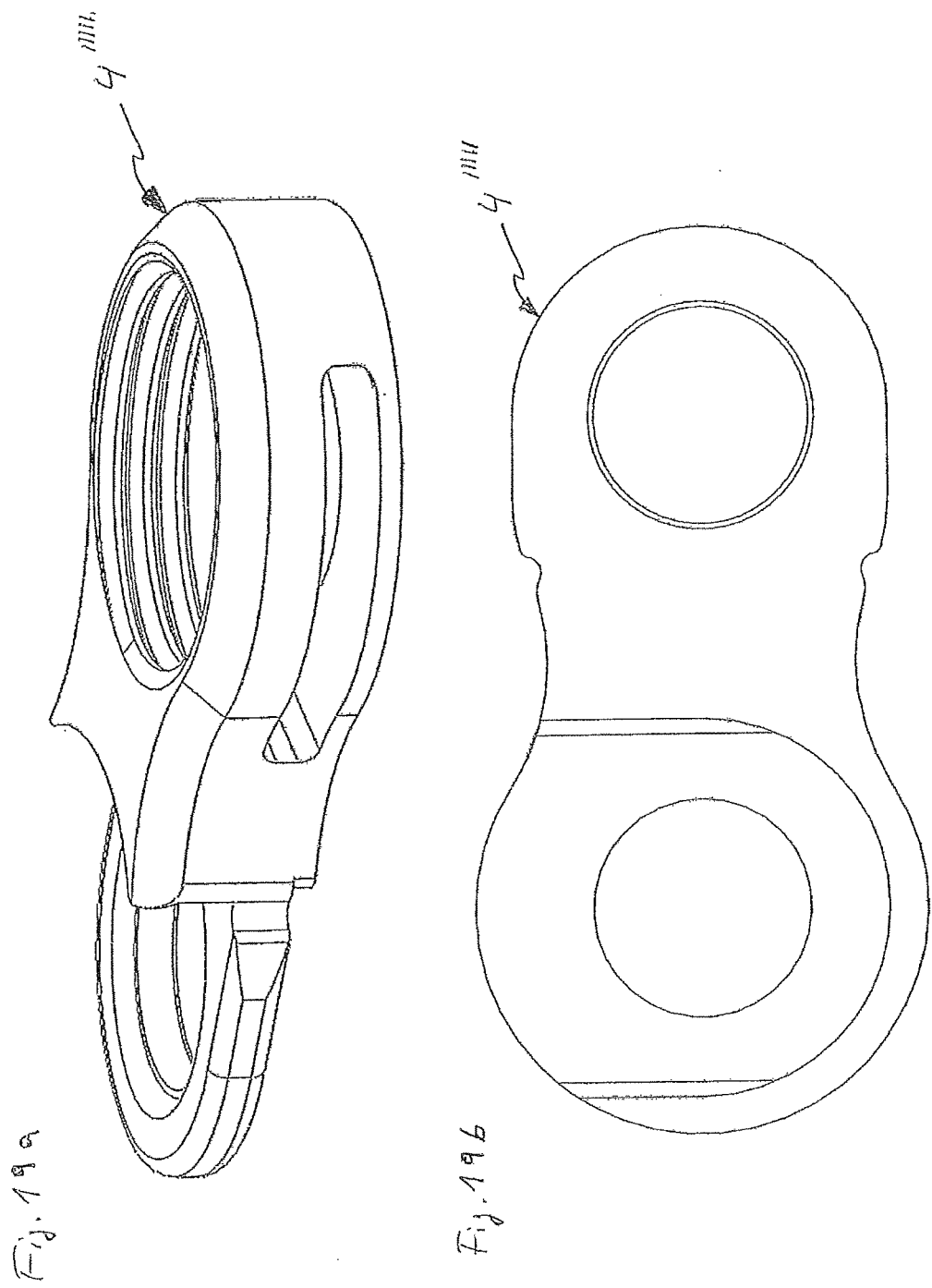

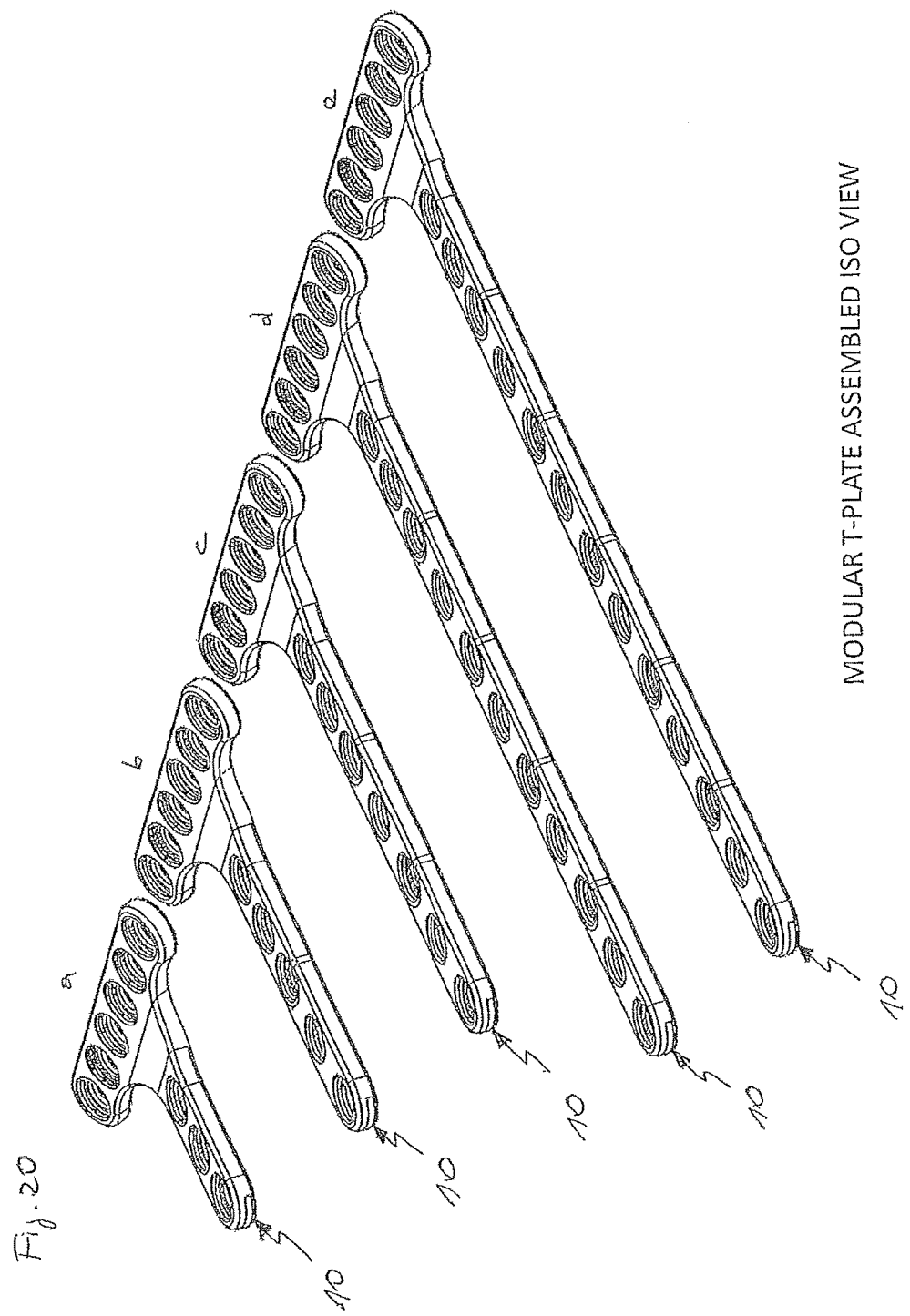

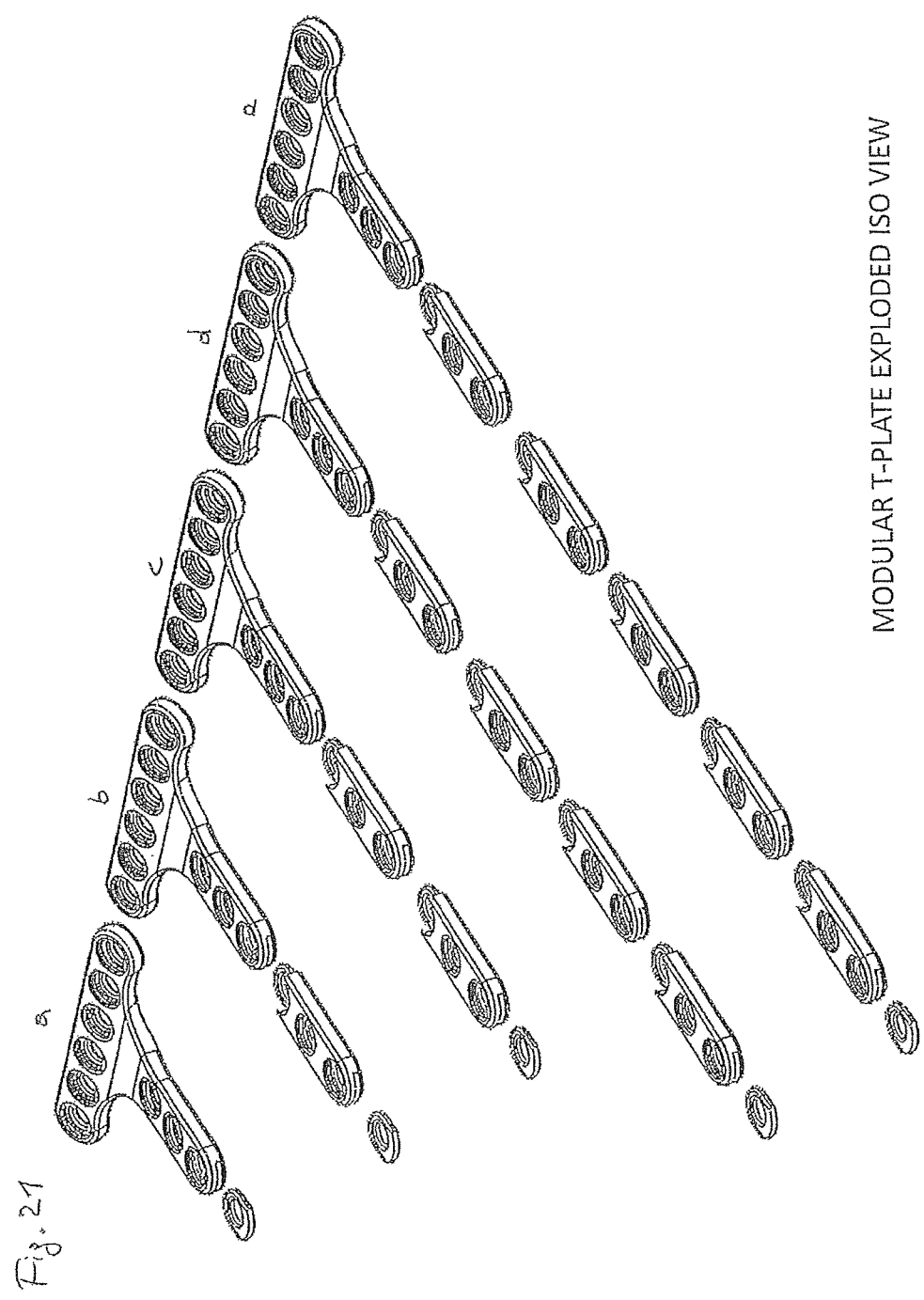

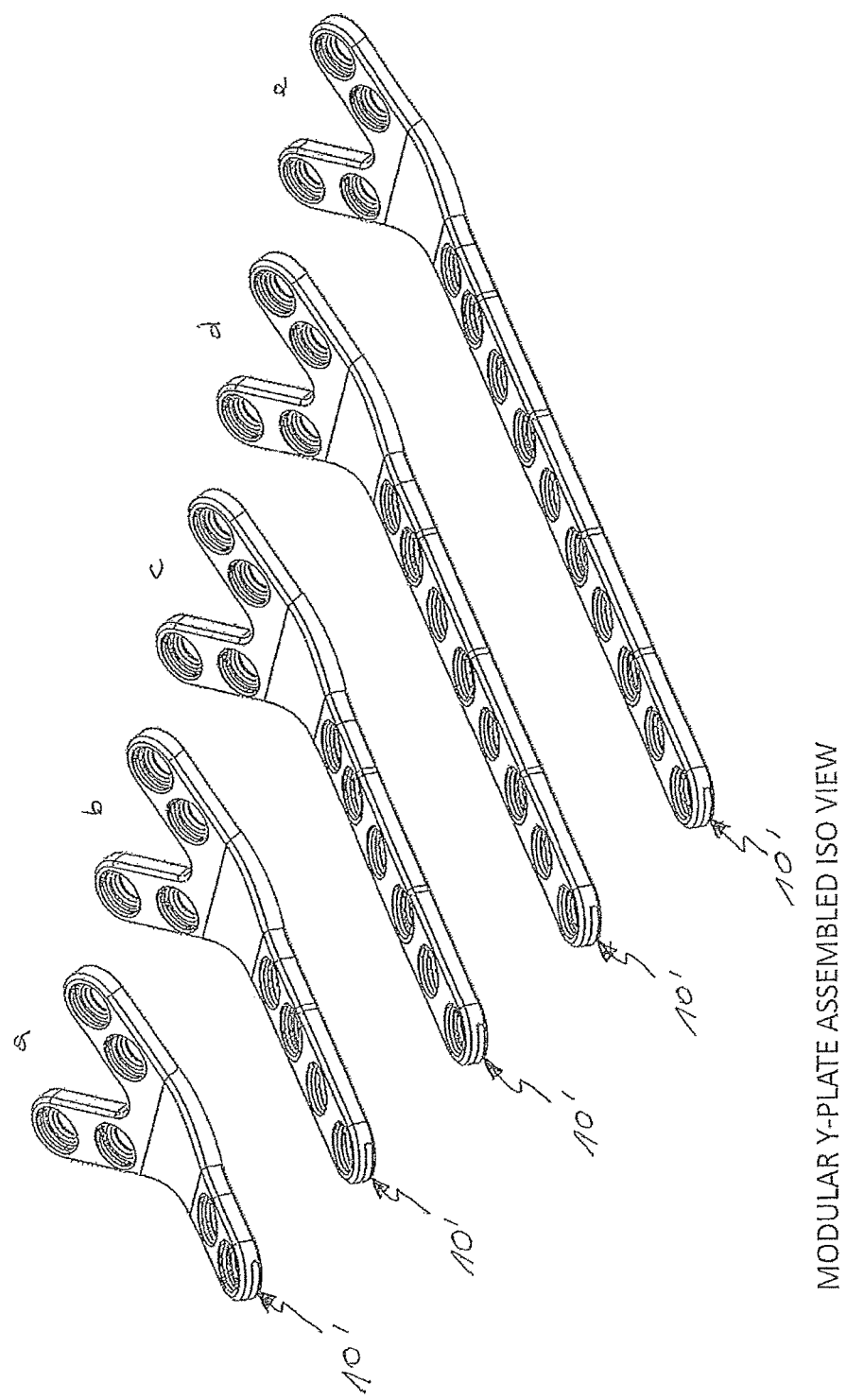
Fig. 22  MODULAR Y-PLATE ASSEMBLED ISO VIEW

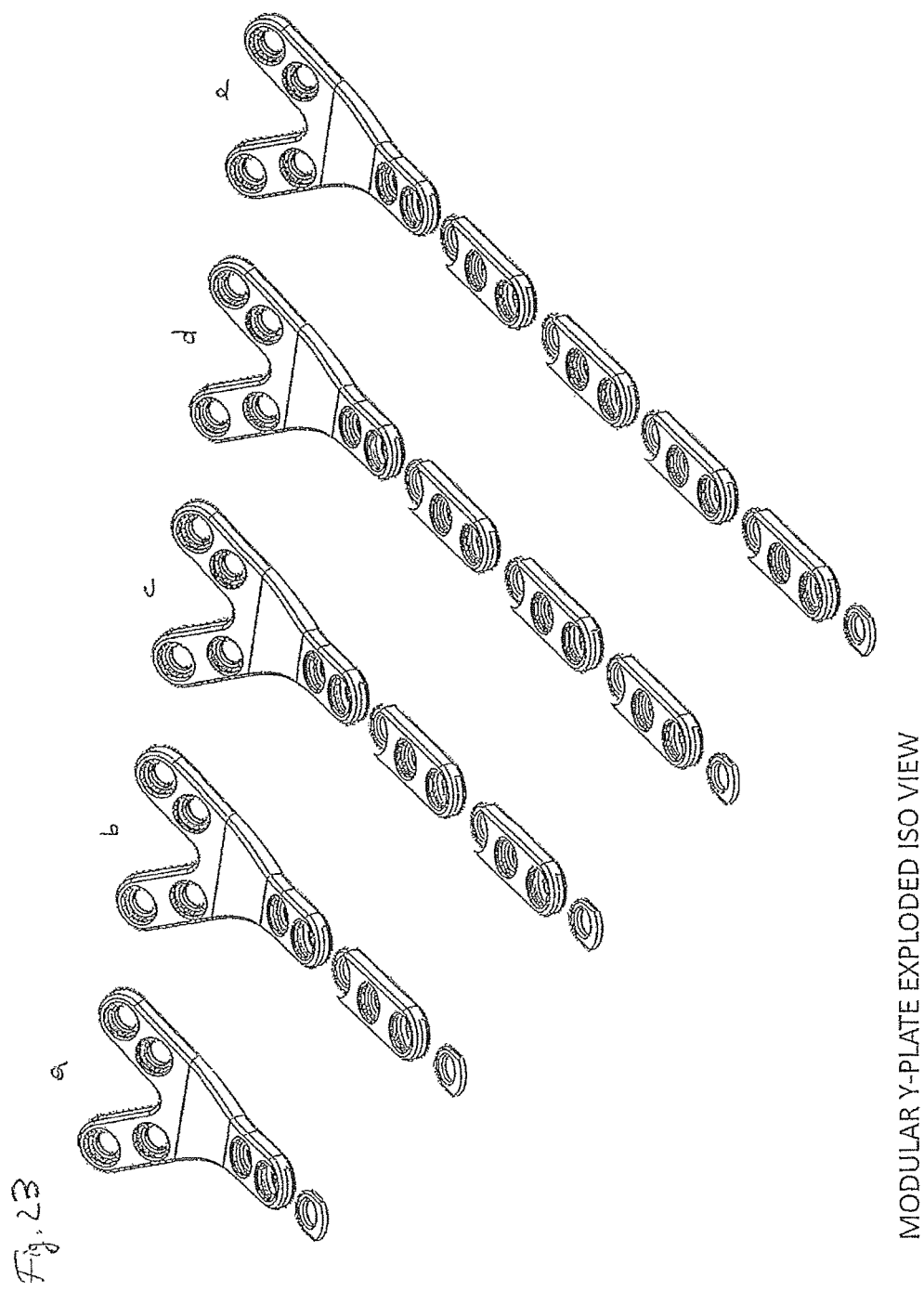

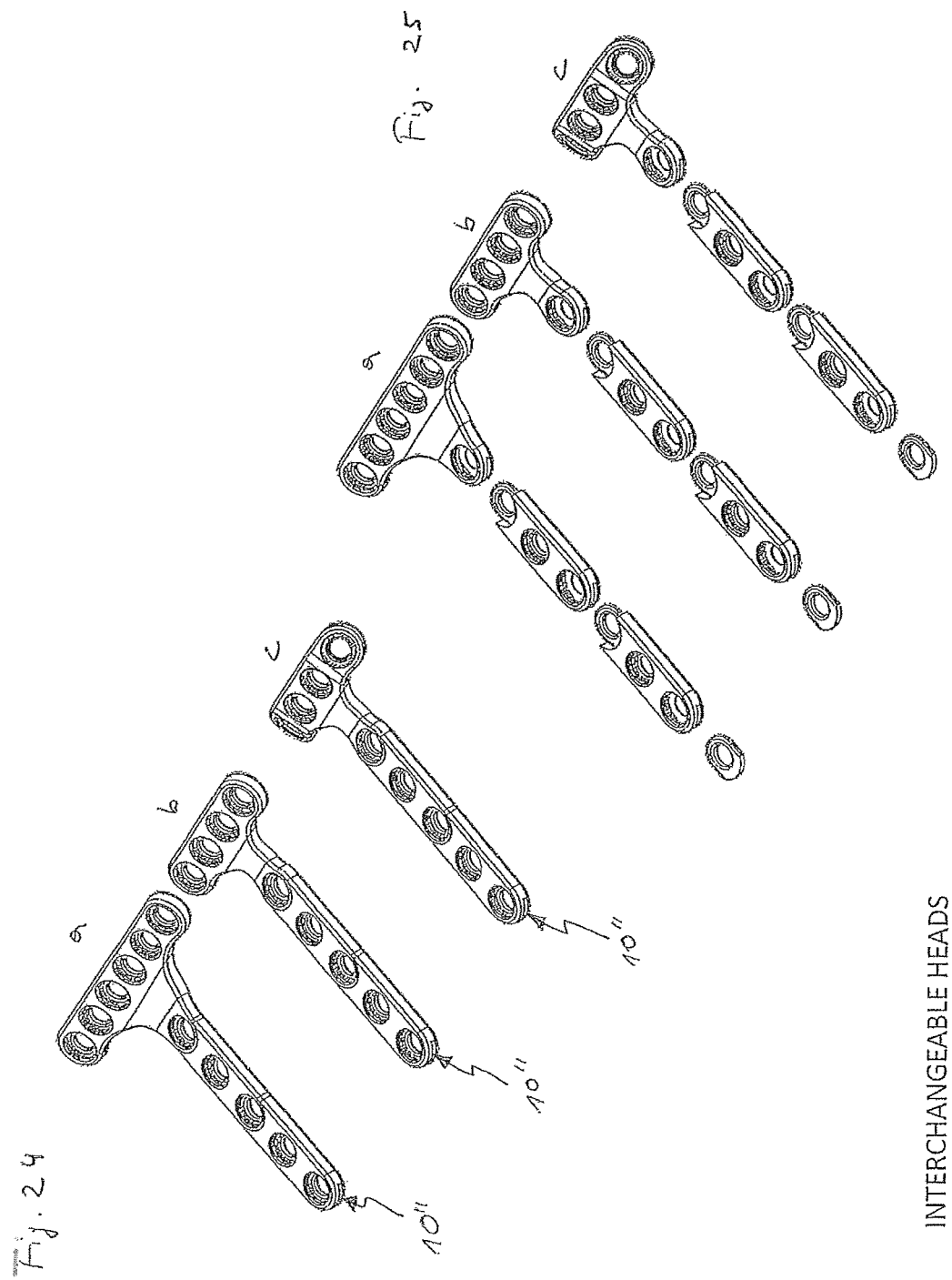

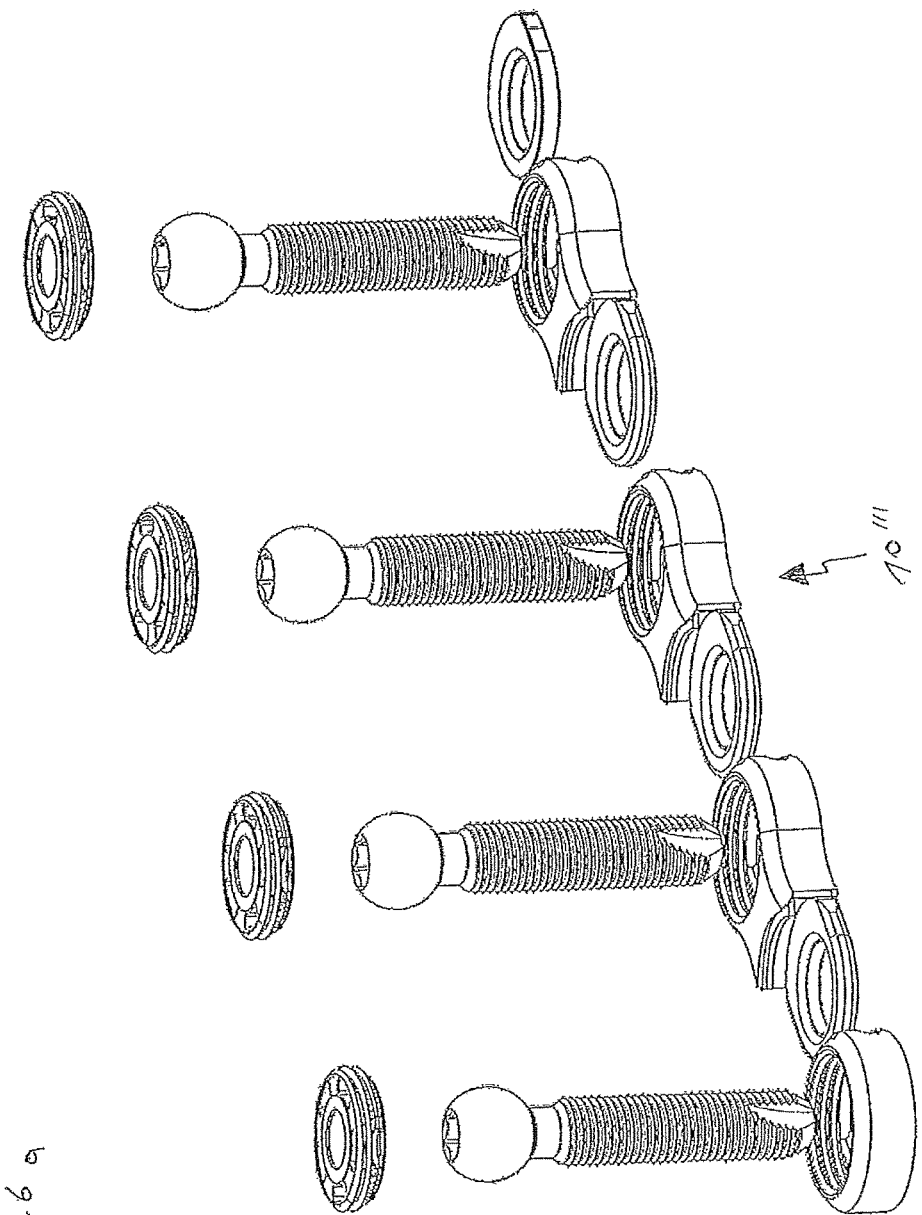

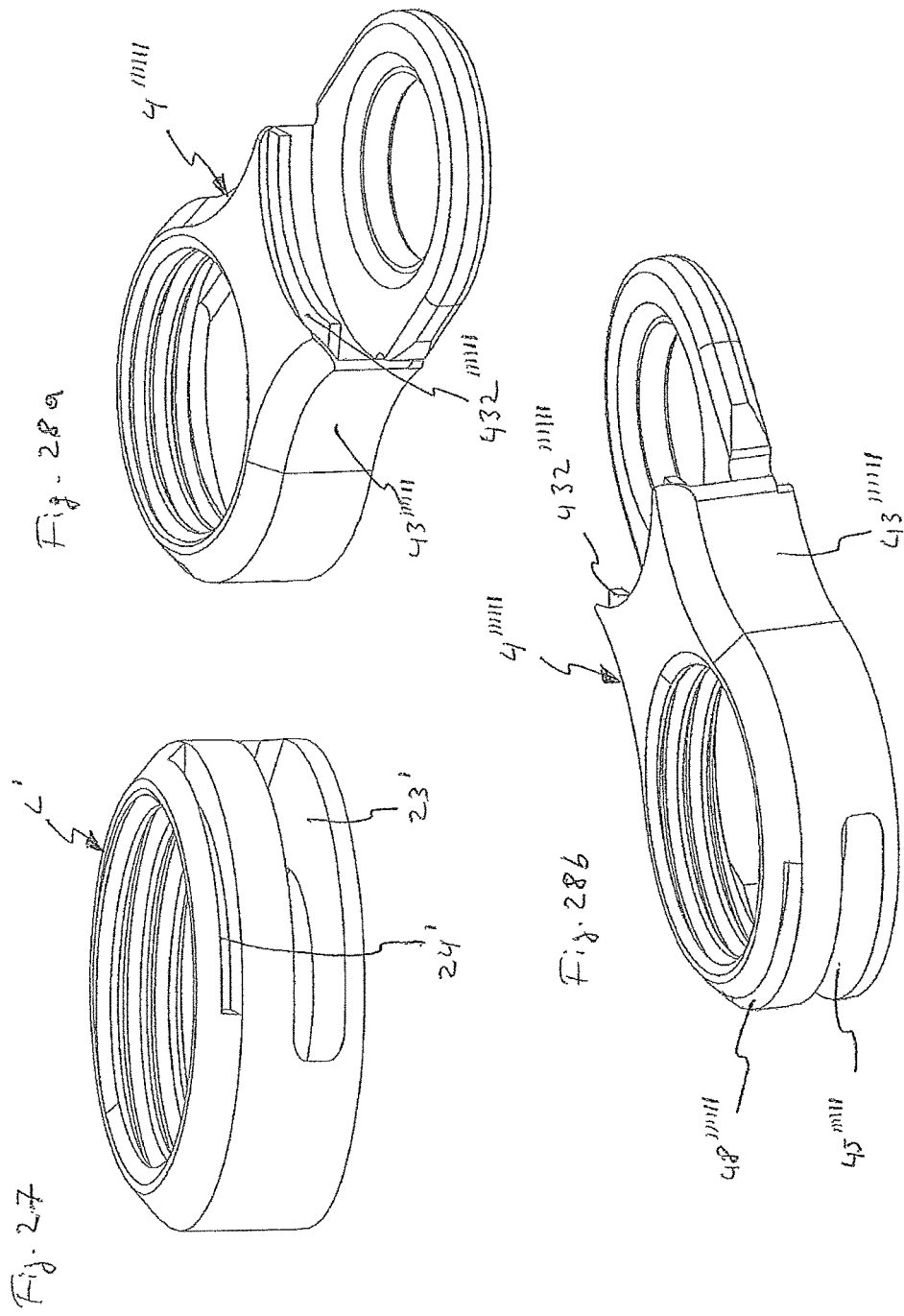

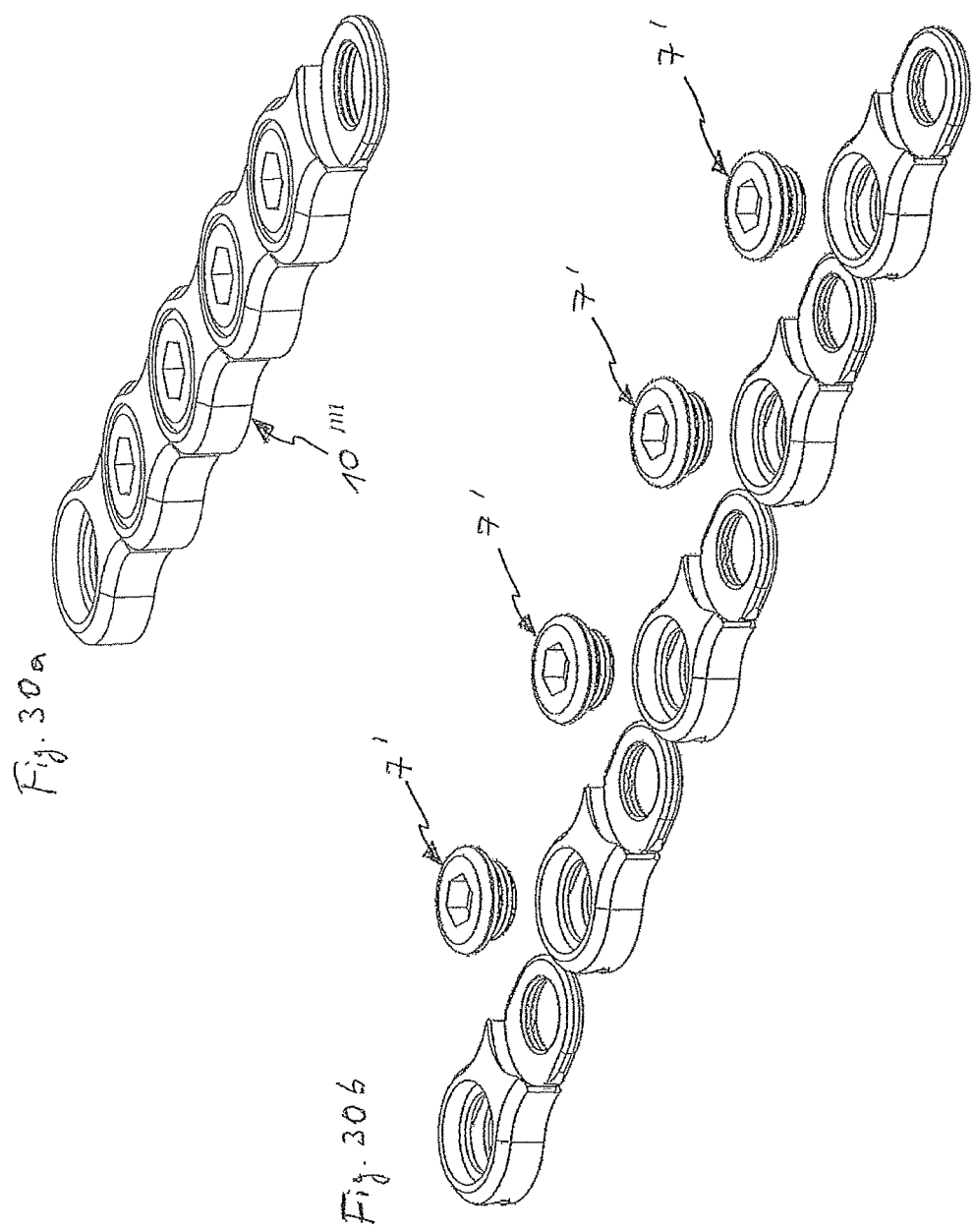

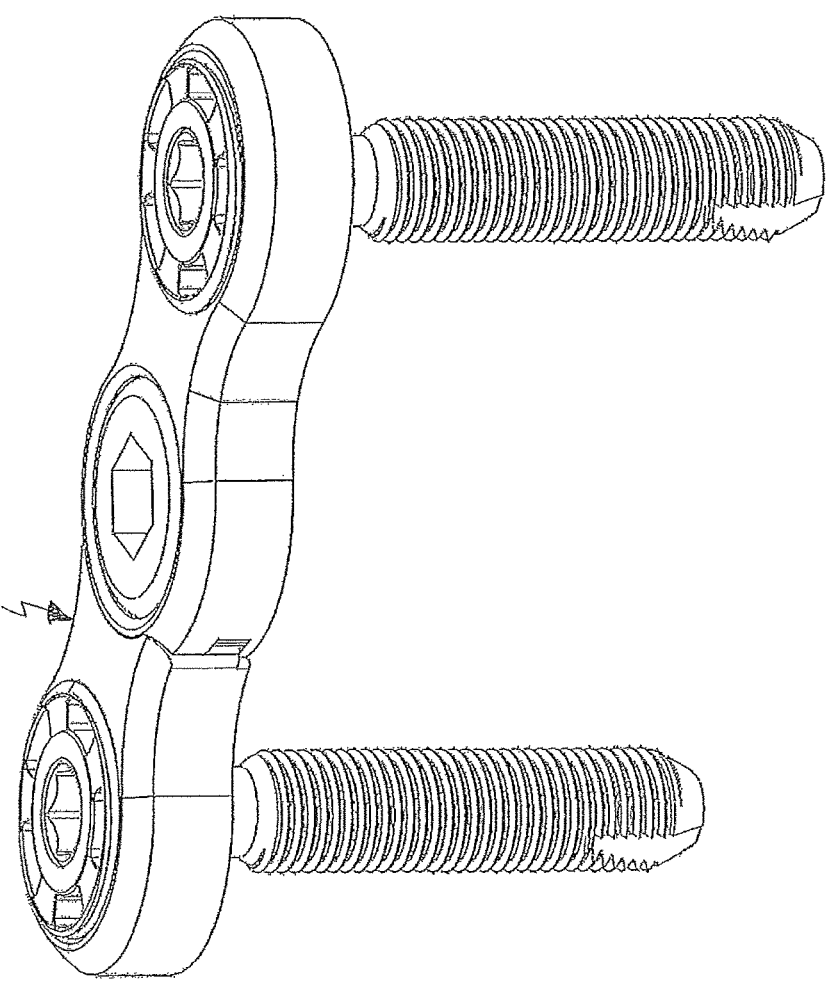

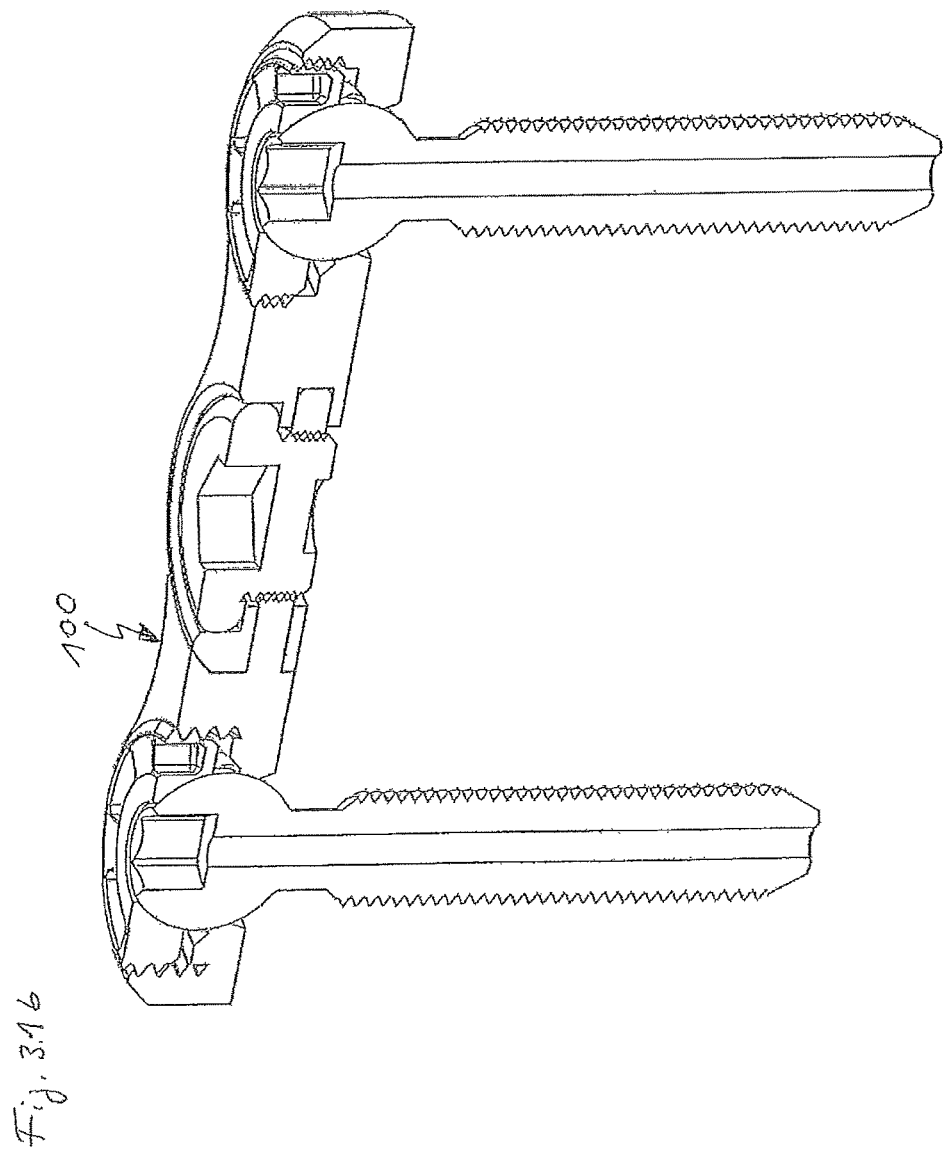
Fig. 3.16

MODULAR BONE PLATE AND CONNECTOR PIECE FOR A MODULAR BONE PLATE

CROSS-REFERENCE TO RELATED APPLICATIONS

This application is a National Phase Patent Application and claims priority to and benefit of International Patent Application Number PCT/IB2012/053035, filed on Jun. 15, 2012, which claims priority to and the benefit of, and wholly incorporates by reference U.S. provisional application No. 61/497,972 to Biedermann filed on Jun. 17, 2011.

FIELD OF THE INVENTION

The invention relates to a modular bone plate and to a connector piece for a modular bone plate.

BACKGROUND OF THE INVENTION

U.S. Pat. No. 5,484,439 describes a modular implant for use in stabilizing femoral bone disorders. In one embodiment the implant has an upper side plate with a widened head and an angled barrel and a lower side plate adapted to be engaged with the upper side plate in a tongue and groove configuration.

SUMMARY OF THE INVENTION

The object underlying the invention is to provide an improved modular bone plate that can be realized for various clinical applications and that is easy to assemble while providing a strong and durable construct.

The object and further developments are addressed by a modular bone plate described according to the various embodiments described herein.

The bone plate according to the invention comprises at least two members each having a top surface and a bottom surface and that can be connected together. The members include a male connection portion with a single hole extending from the top surface to the bottom surface and a female connection portion with a single hole extending from the top surface to the bottom surface. The male connection portion is insertable into the female connection portion so that the holes overlap and wherein an anchor or a plug member is insertable into the holes when they overlap.

By means of the modular construction bone plates according to specific clinical requirements and adapted to a specific anatomical situation can be easily designed.

There is only one hole of engagement in the male connection portion. The engagement portion of the male portion is relatively short. This makes the adjustment and engagement step easy to perform.

The modular bone plate may be designed pivotable such that an angle between the members to be connected can be selected. The members may be locked with respect to each other in the angled configuration.

In a further development there are additional points of engagement realized by a male portion in the female portion and a female portion in the male portion. This allows a more even load distribution between the members to be connected.

Locking and non-locking screws may be used with the modular bone plate. The locking screws make use of a locking cap that is screwed into the hole. This renders the construct more stable and increases the stiffness. The plate portions can be clamped together also without screws using a plug member.

BRIEF DESCRIPTION OF THE DRAWINGS

Further features and advantages of the invention will become apparent from the description of embodiments with reference to the accompanying drawings. In the drawings:

FIG. 1a shows a perspective view of a modular bone plate assembly according to a first embodiment;

FIG. 1b shows an exploded view of the modular bone plate assembly according to the first embodiment;

FIG. 1c shows a cross sectional perspective view of the modular bone plate assembly to the first embodiment;

FIG. 1d shows a cross sectional view of the bone plate assembly according to the first embodiment;

FIG. 2a shows a perspective view of a ball locking cap from the top;

FIG. 2b shows a perspective view of the ball locking cap from the bottom;

FIG. 3a shows a perspective view of a male end piece of the modular bone plate according to the first embodiment;

FIG. 3b shows a perspective view of a female end piece according to a first embodiment;

FIG. 5b shows a cross sectional top view of the modular bone plate assembly according to the second embodiment;

FIG. 6 shows a cross sectional top view of an angled male/female connector piece in a second embodiment;

FIG. 7c shows a cross sectional side view of the modular bone plate assembly according to the third embodiment;

FIG. 7e shows an exploded view of the modular bone plate assembly according to the third embodiment;

FIG. 8a shows a perspective view of the female/male connector piece (4.5 mm to 2.5 mm) according to a third embodiment;

FIG. 8b shows a side view of the female/male connector piece (4.5 mm to 2.5 mm) according to a third embodiment;

FIG. 10a shows a perspective view of a modular bone plate assembly according to a fourth embodiment;

FIG. 10b shows a side view of the modular bone plate assembly according to the fourth embodiment;

FIG. 11a-e show perspective views of a humerus expandable plate according to a fifth embodiment;

FIG. 12a-e show exploded views of the humerus expandable plate according to the fifth embodiment;

FIG. 13a-e show perspective top views of the humerus expandable plate according to the fifth embodiment;

FIG. 14a-e show perspective bottom views of the humerus expandable plate according to the fifth embodiment;

FIG. 15 shows a top view of a modular hard angle bone plate according to a sixth embodiment;

FIG. 16a-i show top views of hard angle connector pieces having angles from 0° to 90°;

FIG. 17a-i show perspective views of hard angle connector pieces shown in FIG. 16a-i;

FIG. 18a shows a perspective view of a female/male connector piece according to a fifth embodiment (angle 45°);

FIG. 18b shows a cross sectional top view of the female/male connector piece according to the fifth embodiment (angle 45°);

FIG. 19a shows a perspective view of a female/male connector piece in a sixth embodiment (angle 90°);

FIG. 19b shows a cross sectional top view of the female/male connector piece in the sixth embodiment (angle 90°);

FIG. 20a-e show perspective views of a modular T-plate according to a seventh embodiment;

FIG. 21a-e show exploded views of the modular T-plate according to the seventh embodiment;

FIG. 22a-e show perspective views of a modular Y-plate according to an eighth embodiment;

FIG. 23a-e show exploded views of the modular Y-plate according to the eighth embodiment;

FIG. 24a-c show perspective front views of a modular bone plate having interchangeable heads according to a ninth embodiment;

FIG. 25a-c show exploded views of the modular bone plate according to the ninth embodiment;

FIG. 27 shows a perspective view of a double latch connector according to the second embodiment;

FIG. 28a shows a perspective view of a female/male connector according to a seventh embodiment in a first orientation;

FIG. 28b shows a perspective view of the female/male connector according to the seventh embodiment in a second orientation;

FIG. 30b shows an exploded view of the modular bone plate according to the eleventh embodiment;

FIG. 30c shows a cross sectional perspective view of the modular bone plate according to the eleventh embodiment;

FIG. 31a shows a perspective view of a modular bone plate assembly according to the eleventh embodiment;

FIG. 31b shows a cross sectional perspective view of the modular bone plate assembly according to the eleventh embodiment;

DETAILED DESCRIPTION OF THE INVENTION

Figure 4:
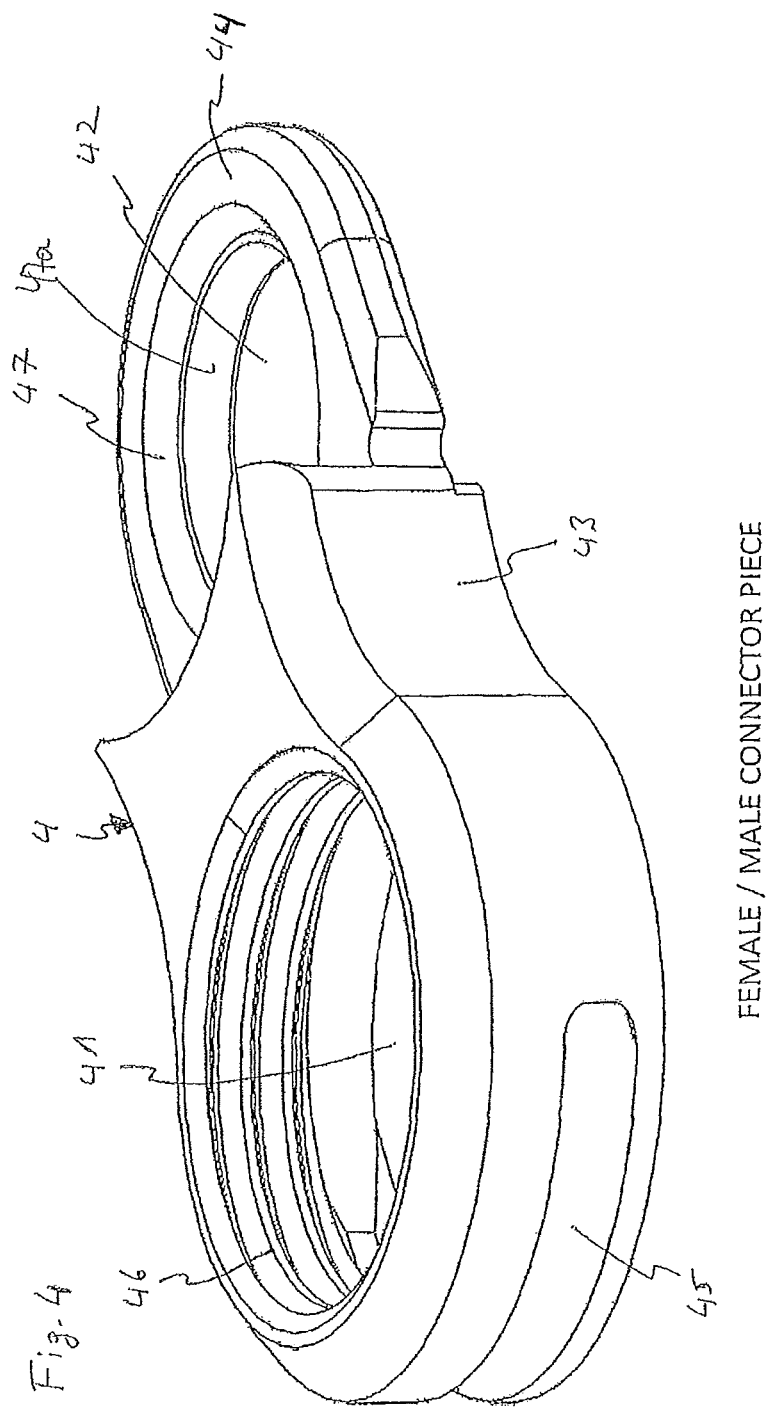
FIG. 4 shows a perspective view of a female/male connector piece according to a first embodiment.

A first embodiment of the modular bone plate assembly will now be described with reference to FIGS. 1 to 4. As can be seen in particular in FIGS. 1a to 1d, the modular bone plate assembly includes a plate member 1 having a top side 1a and a bottom side 1b. The modular bone plate 1 comprises a female end piece 2 (see FIG. 3b), a male end piece 3 (see FIG. 3a) and referring to FIGS. 1a to 1d, a plurality of female/male connector pieces 4 (see FIG. 4).

The modular bone plate assembly 1 further comprises bone anchoring elements, for example—bone screws 5 having a threaded shank 51 for anchoring the bone anchoring element 5 in a bone and a substantially ball-shaped head 52 with an engagement structure 55 for engagement with a tool, for example a screwdriver. It is also possible to provide other bone anchors, for example bone nails having a threadless shank or having barbs. Furthermore, the bone anchoring element 5 may comprise a through bore hole 54 i.e. a channel (see FIG. 1c) for inserting, for example, bone cement. Further, a substantially cylindrical insert 6 is provided having an outer thread which is adapted to fit with an inner thread of the female end piece 2 or a female connection portion or female part of the female/male connector piece 4. The outer thread may also fit with an inner thread of the male end piece 3 (not shown) or a male connection portion or male part of the female/male connector piece 4 (not shown). The insert functions as a locking cap or locking element for locking the head 52 of the bone screw 5.

The male end piece 3 which is substantially formed by a plate comprises a through hole 31, the female end piece 2 comprises a through hole 21 and the female/male connector piece comprises a first through hole 41 and a second through hole 42 (see FIGS. 3a to 4). The through hole 31, the through hole 21, the through hole 41 and the through hole 42 have to be understood as circumferentially closed openings.

The female end piece 2 is substantially cylindrical and the hole 21 comprises a portion 22 with an internal thread. Further, the female end piece 2 comprises a recess 23 which is provided in the side wall of the female end piece 2 and is in communication with the hole 21. The recess 23 extends about the half of the circumference of the side wall of a female end piece 2 and is adapted to accommodate the male portion of the female/male connector piece 4. The recess 23 extends from the outside into the hole 21. Thereby a lug or pocket is formed which is adapted to engage a male portion having a tongue or projection.

The main body of the male end piece 3 is substantially cylindrical and has an extension 32 to one side adapted to the contour of the recess 23 of the female end piece 2. The extension 32 may be formed as tongue or projection which is adapted to engage a female portion having a recess, a lug or a pocket. A portion 33 of the hole 31 of the male end piece 3 is beveled and therefore conical on the top side. Further, a spherical bottom seat 34 is provided for accommodating the head 52 of the bone screw 5.

The female/male connector piece 4 is an integral combination of the male end piece 3 and the female end piece 2 connected by a middle portion 43. The female connection portion of the female/male connector piece 4 hereby comprises a through hole 41 having an inner thread 46 and a recess 45 extending about the half of the circumference of the sidewall of the female connection portion of the female/ male connector piece 4. The recess 45 is in communication with the hole 41. The male connection portion of the female/male connector piece 4 is formed by a lug portion 44 having a through hole 42 in its middle. The hole 42 has a circumferential beveled portion 47 as the beveled portion 33 of the male end piece 3 and a spherical bottom seat 47*a* as the spherical bottom seat 34 of the male end piece 3.

As can be seen in FIG. 1*a* to FIG. 1*c*, the recess 23 of the female end piece 2 or the recess 45 of the female/male connector piece 4 serves for accommodating the male end piece 3 or the male connection portion of the female/male connector piece 4 such that in an assembled state the respective holes of male and female connection portions overlap.

The extended side 32 of the male end piece 3 is adapted to fit into the recess 23 of the female end piece or the recess 45 of the female/male connector piece. Thereby, the portion 32 of the male end piece 3 or the male portion 44 of the female/male connector piece 4 serves as a tongue portion 32, 44 and the recess 23 of the female end piece 3 or the recess 45 of the female/male connector piece 4 serves as a lug portion 23, 45, respectively. When the male portion is inserted into the female portion, it forms a seat for the ball-shaped head 52 of the bone screw 5 that allows orientation of the bone screw 5 at an angle with respect to the straight position, as shown for example in FIG. 1*a*.

As can be seen from FIG. 1*b* and FIG. 1*c* referring to the modular bone plate assembly 1, three female/male connector pieces 4, one female end piece 2, and one male end piece 3 are connected to each other. The loose connection of these parts is locked by the bone anchoring elements 5. The threaded shaft 51 of the bone anchoring element 5 extends through the hole 31 of the male end piece 3 or the hole 42 of the female/male connector piece 4 or through the hole 41 of the female/male connector piece 4 and the hole 42 of a further female/male connector piece 4 or through the hole 42 of the female/male connector piece 4 and the hole 21 of the female end piece 2. The lower area of the screw head 52 thereby contacts the spherical portion 34 of the male end piece 3 or the spherical portion 47*a* of the male portion of the female/male connector piece 4. By contacting the spherical portion 34 or 47*a* on the one hand and the inner portion of the hole 21, i.e. the inner thread of the female end piece 2 or the inner surface 41, i.e. the inner thread of the female portion of the female/male connector piece 4 on the other hand, both portions are centered by the bone anchoring element 5 or another locking element (see FIG. 2*a, b*).

A further possibility to lock the female parts and the male parts to each other is to provide a ball locking cap 7, as can be seen from FIG. 2*a* and FIG. 2*b*. The ball locking cap 7 comprises an upper threaded portion 71 and a lower rounded substantially spherical portion 72 which is adapted to cooperate with the spherical portions 34 of the male end piece 3 or the spherical portion 47*a* of the female/male connector piece 4. The rounded portion 72 thereby substitutes the lower portion of the head 52 of the bone screw 5 and ensures the centering function as described above. The ball locking cap 7 further comprises an engagement portion 73 for being engaged by a tool to screw the ball locking cap 7 into the inner thread 22 of the female end piece of the inner thread 46 of the female/male connector piece or the inner thread 22 of the female end piece 2.

Figure 5A:
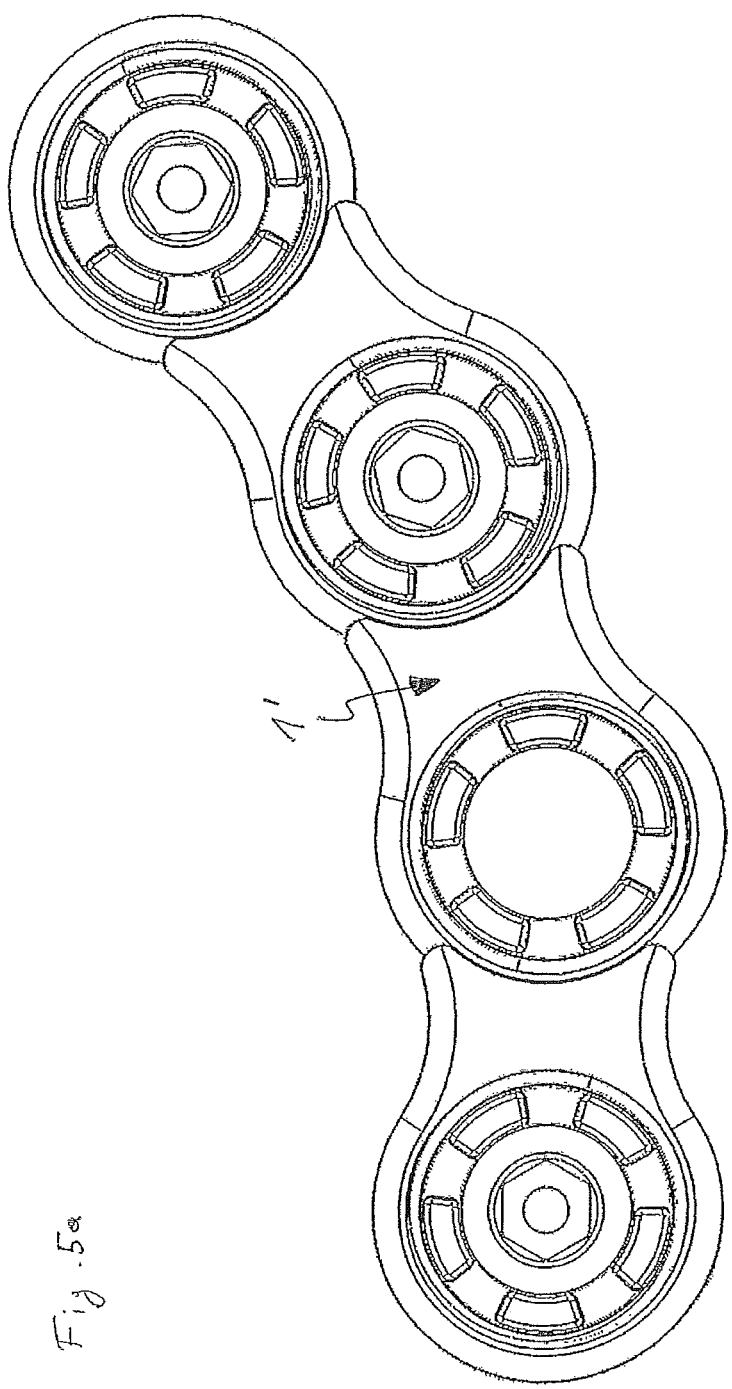
FIG. 5a shows a top view of a modular bone plate assembly in a second angled embodiment that has an angled configuration.
Figure 7A:
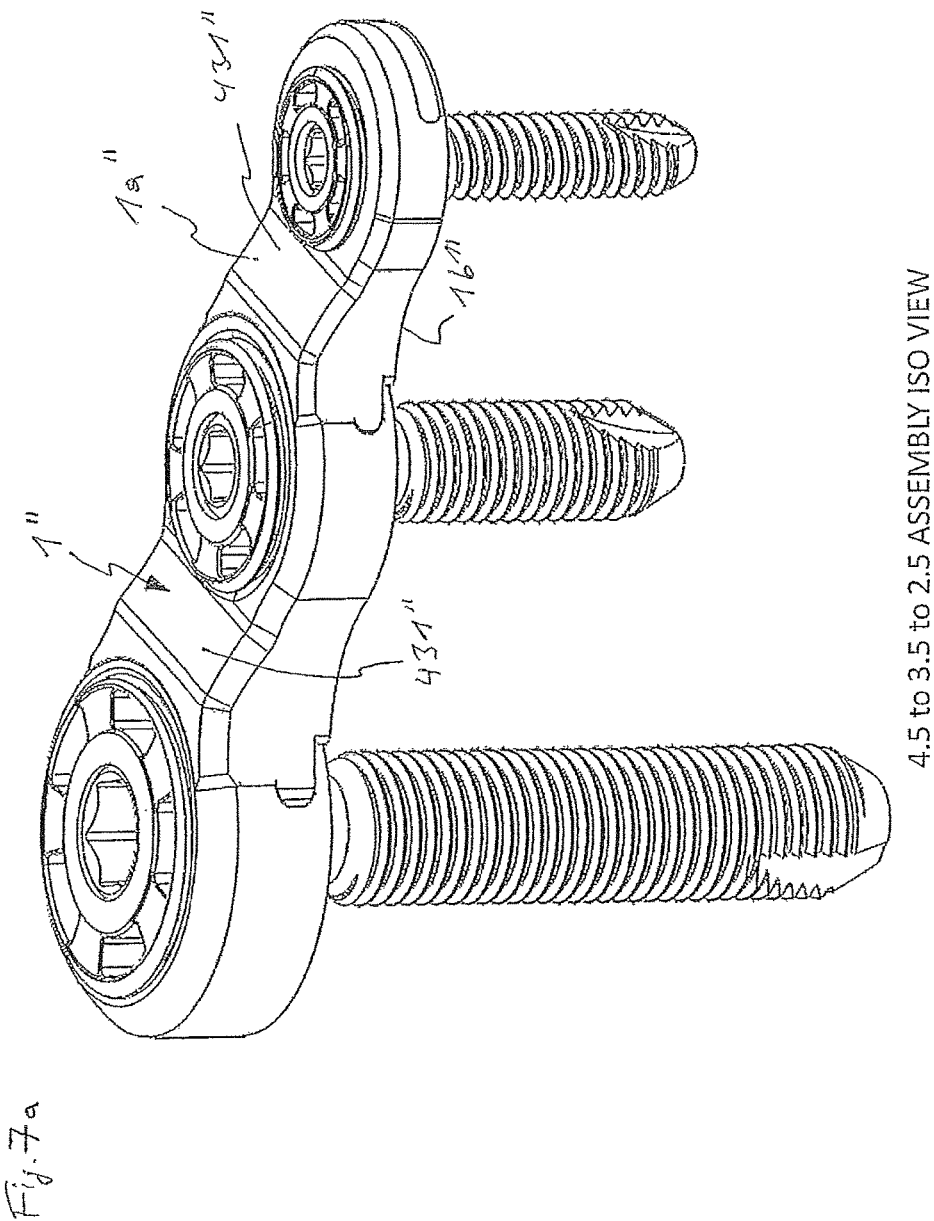
FIG. 7a shows a perspective view of a modular bone plate system according to a third embodiment.
Figure 7B:
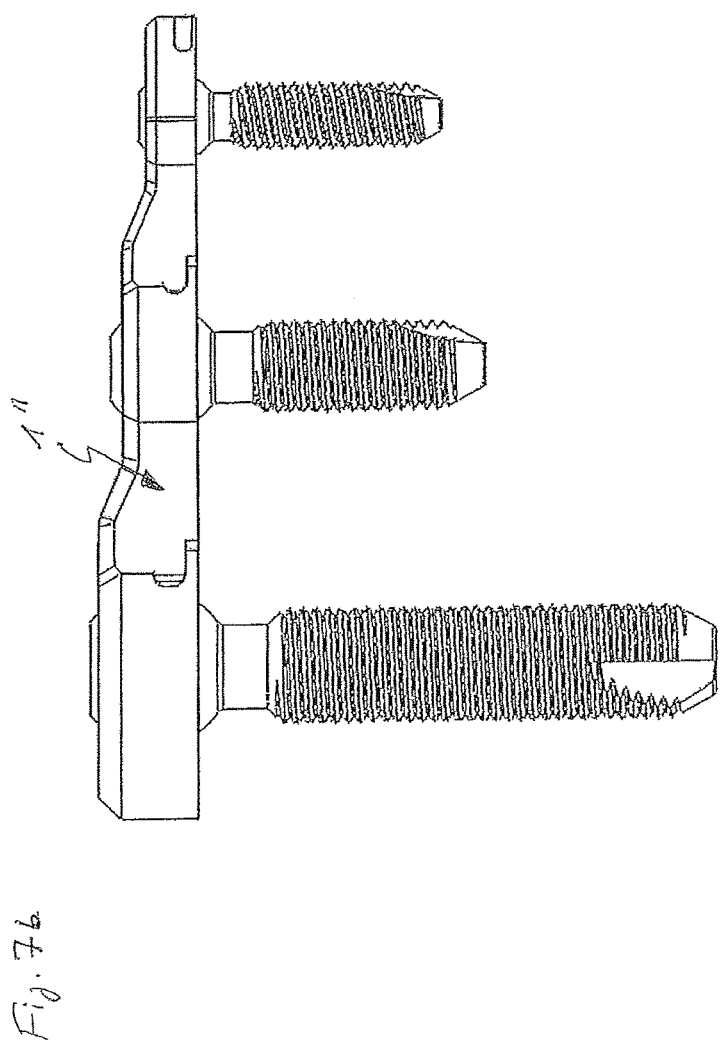
FIG. 7b shows a side view of the modular bone plate assembly according to the third embodiment.
Figure 7D:
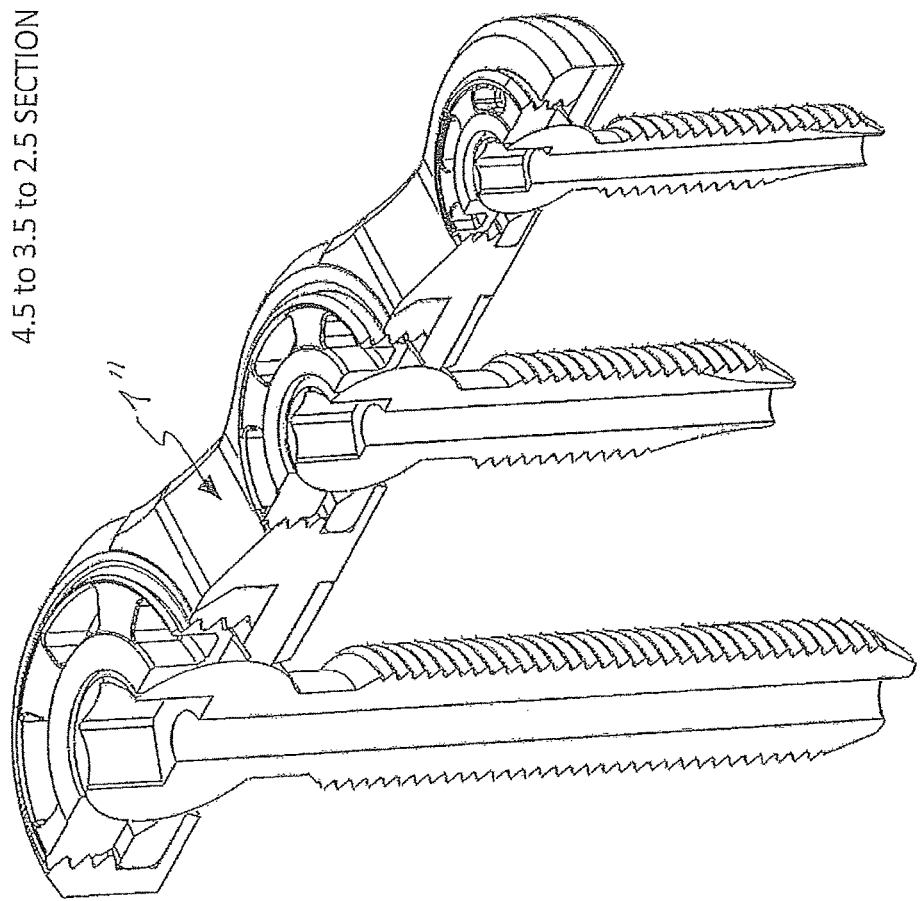
FIG. 7d shows a cross sectional perspective view of the modular bone plate assembly according to the third embodiment.

A second embodiment of the modular bone plate assembly will now be described with reference to FIGS. 5*a* to 6. As can be seen in particular in FIG. 5*a* and FIG. 5*b* the modular bone plate has an angled configuration. Referring to FIG. 6 the tongue portion 44 of the female/male connector piece 4' in the second embodiment is identical to the tongue portion 44 of the female/male connector piece 4 in the first embodiment. As can be seen in particular in FIG. 6 the lug portion 45' which is adapted to accommodate the tongue portion 44' or the male end piece 3 comprises a circular portion 45*a*' and two straight portions 45*b*' that include an angle with respect to each other, which is about 40° in this embodiment. Other angles are also suitable here, for example 10°, 90° or 120°. In FIG. 6 the angle between the straight portions 45*b*' and a middle axis of the female/male connector piece 4' are each 20°. But these two angles may also be different from each other to define a preferred orientation.

By this configuration the female/male connector pieces 4' which are connected to each other can be rotated relative to each other in a plane parallel to the surface of the modular bone plate to achieve an angled configuration.

A third embodiment of the modular bone plate assembly will now be described with reference to FIGS. 7*a* to 9*b*. The modular bone plate 1" is provided in a cascaded form. Referring to FIGS. 7*a* to 7*d* the modular bone plate 1" as a whole decreases in thickness from the left side of the Figures towards the right side of the Figures. Only the top surface 1*a*" of the modular bone plate 1" is lowered referring to FIG. 7*a* in two steps by means of two inclined portions 431" of the female/male connector pieces 4", which can be seen in FIG. 7*e*.

As can be seen from FIGS. 8*a* and 8*b*, the female/male connector piece 4" according to the third embodiment differs from the first embodiment in that the middle portion 43" comprises an inclined portion 431" which is provided on the top side of the middle portion 43" and in that the diameters of the two holes provided at the male and female connection portions of the female/male connector piece 4" differ from each other. As in the first embodiment the female connection portion of the female/male connector piece 4 hereby comprises a through hole 41" having an inner thread 46" and a recess 45" extending about the half of the circumference of the sidewall of the female connection portion of the female/male connector piece 4". The recess 45" is in communication with the hole 41". The male connection portion of the female/male connector piece 4" is formed by a lug portion 44" having a through hole 42" in its middle. The male and female connection portions of the female/male connector piece 4" may be formed according to the corresponding portions according to the first embodiment.

Figure 9A:
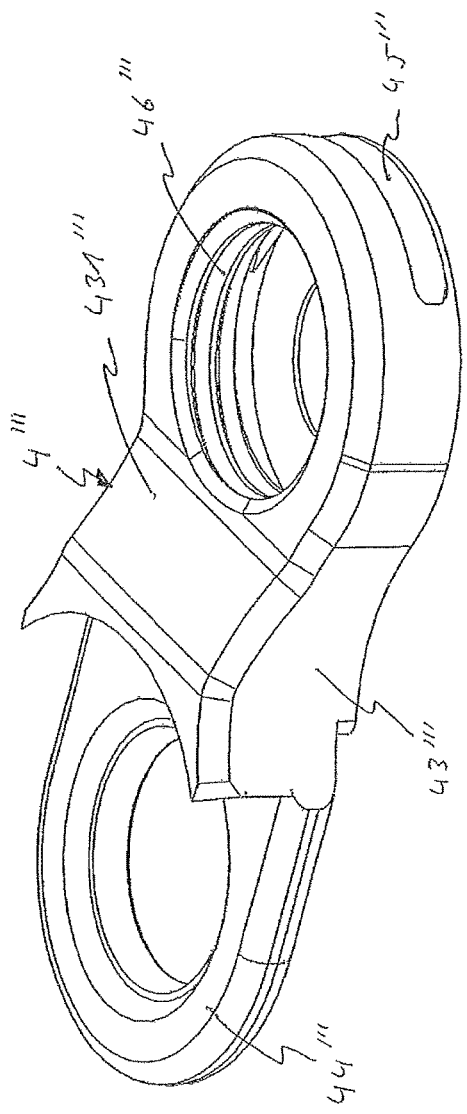
FIG. 9a shows a perspective view of the female/male connector piece (3.5 mm to 2.5 mm) according to a fourth embodiment.
Figure 9B:
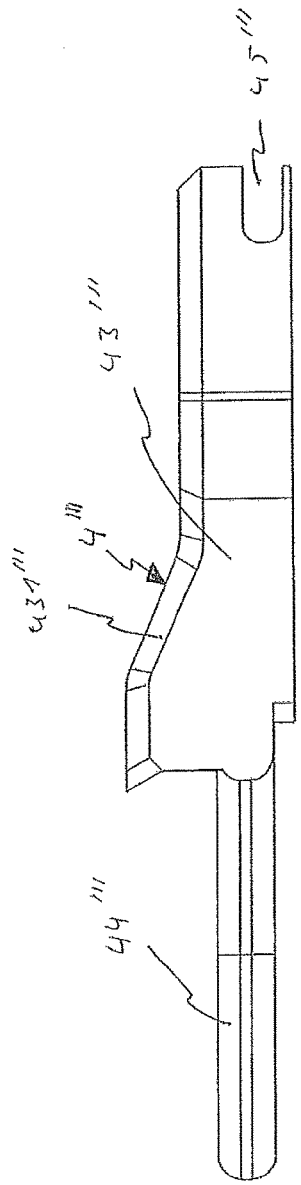
FIG. 9b shows a side view of the female/male connector piece (3.5 mm to 2.5 mm) according to a fourth embodiment.
Figure 26:
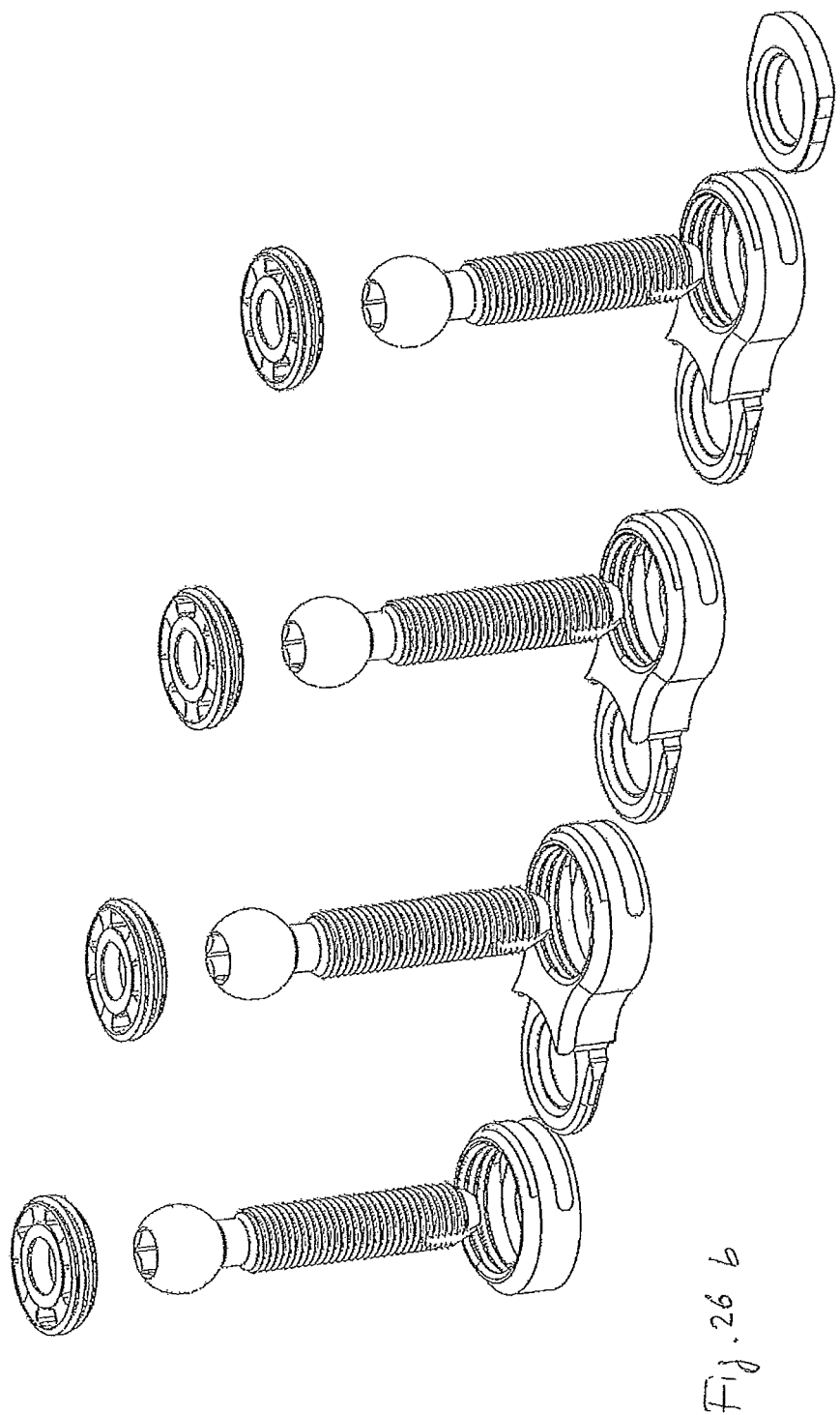
FIG. 26a shows a perspective view of a modular bone plate assembly according to a tenth embodiment in a first orientation.
FIG. 26b shows a perspective view of the modular bone plate assembly according to a tenth embodiment in a second orientation.
Figure 29:
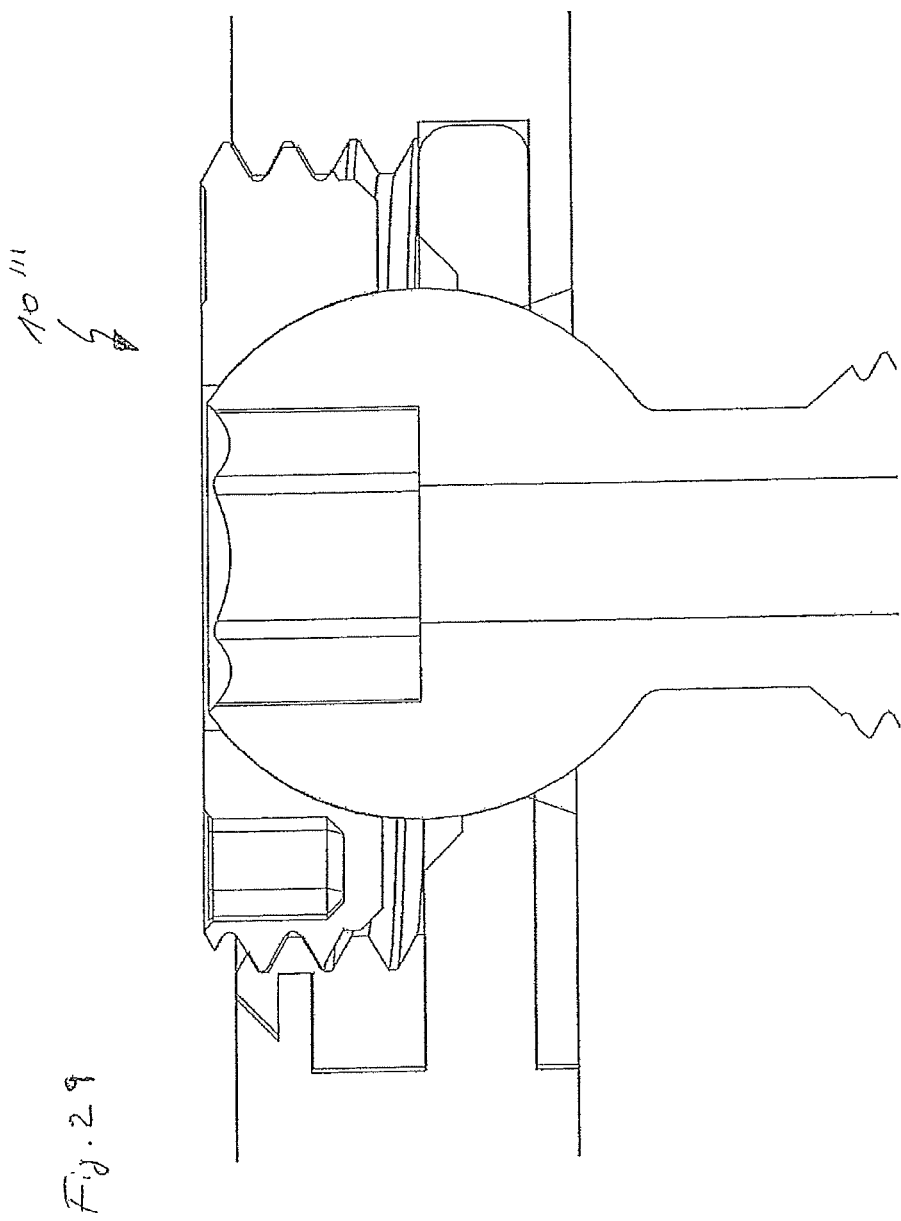
FIG. 29 shows a cross sectional side view of the modular bone plate assembly according to the tenth embodiment.

As can be seen from FIGS. 9*a* and 9*b*, the female/male connector pieces 4" and 4'" only differ from each other by the dimensions. The female/male connector piece 4" is a 4.5 mm to 3.5 mm connector; the female/male connector piece 4'" is a 3.5 mm to 2.5 mm connector, as can be seen in FIGS. 9*a*, 9*b*. These mm-values refer to the diameter of the holes. Therefore, this bone plate can be used with screws having different shaft diameters and/or head diameters.

A fourth embodiment of the modular bone plate assembly will be described referring to FIGS. 10*a* to 10*b*. The modular bone plate 1'" according to the fourth embodiment is also provided in a cascaded form. Opposite to the third embodiment referred to in FIG. 10*a* the modular bone plate 1'" decreases in thickness from the center of the bone plate towards either side by means of inclined portions 431'" corresponding to the inclined portions 431" according to the third embodiment.

A fifth embodiment of the modular bone plate assembly is described with reference to the FIGS. 11 to 14. The plate is a humerus expandable plate 1"".

By the modular system, the length of the modular bone plate 1"" can be chosen as desired. As can be seen in particular from FIG. 12*a-e* the modular bone plate 1"" comprises a main body having a plurality of holes for connecting the plate to a bone and none (a), one (b), two (c), three (d) or four (e) female/male connector pieces having a middle portion comprising a hole and one male end piece 3"". With this system it is possible to combine one type of head with a plurality of connector pieces to provide a plate with a desired length. As can be seen from FIG. 13, the thickness of the main body or of the bone plate may vary or as can be seen from FIG. 14, the main body may be bent or angled.

A sixth embodiment of the modular bone plate assembly will be described with reference to FIGS. 15 to 19*b*. The modular bone plate 1"" is a hard angle construct or fixed angle construct. The modular bone plate 1"" is a combination of the pieces shown in FIG. 16*a-i* and FIG. 17*a-i* is referring to the parts shown in FIG. 16 and FIG. 17, FIG. 16*a* corresponds to FIG. 17*i*, FIG. 16*b* corresponds to FIG. 17*h*, FIG. 16*c* corresponds to FIG. 17*g*, FIG. 16*d* corresponds to FIG. 17*f*, FIG. 16*e* corresponds to FIG. 17*e*, FIG. 16*f* corresponds to FIG. 17*d*, FIG. 16*g* corresponds to FIG. 17*c*, FIG. 16*h* corresponds to FIG. 17*b* and FIG. 16*i* corresponds to FIG. 17*a*. The angled construction is achieved, as shown in FIGS. 18 to 19 by providing the recess 45"" in the female portion into which the male portion is inserted at an angle with respect to the longitudinal axis of the connector pieces.

The angles 0° (FIGS. 16*e*; 17*e*), 30° (FIGS. 16*d, f*; 17*d, f*), 45° (FIGS. 16*c, g*; 17*c, g*), 60° (FIGS. 16*b, h*; 17*b, h*) and 90° (FIGS. 16*a, i*; 17*a, i*) are shown. Other angles are also possible. By connecting these parts according to the above mentioned lug-tongue-principle a configuration shown in FIG. 15 is achievable. The configuration is locked by bone screws or with ball locking caps as described above. In a further modification, the female portion may also have in addition the angled construction according to FIGS. 5 to 6 that allow variations from the fixed angle. As can be seen from FIGS. 18*a, b* and 19*a, b*, the angled configuration is achieved by providing the recess 45"" of the female connection portion of the female/male connector piece 4"" at the desired position at the circumference of the outer wall of the female connection portion. FIGS. 19*a, b* show the 90° angle version as shown in FIGS. 16*a, i* and 17*a, i*.

A seventh embodiment of the modular bone plate assembly is shown in FIGS. 20 and 21. The bone plate is a T-plate with a T-shaped head, applicable for example, to the wrist. The plate as a whole may be constructed in an angled or bent way.

An eighth embodiment of the modular bone plate assembly is shown in FIGS. 22 and 23. The bone plate is a Y-plate with a Y-shaped head, applicable, for example, to the elbow.

A ninth embodiment of the modular bone plate assembly will be described with reference to the FIGS. 24 and 25. The only difference referring to the other embodiments is the exchangeable head which can be seen in FIG. 24*a-c* for example. In FIG. 24*a* a straight head with six holes, in FIG. 24*b* a straight head having four holes and in FIG. 24*c* a head having four holes two of which are inclined are shown.

A tenth embodiment of the modular bone plate assembly 10''' is shown in FIG. 26*a* to FIG. 29.

As can be seen from FIGS. 27 to 28*b* the connection between the male and female part is realised by a double latch connector. The female connecting piece 2' according to a second embodiment comprises the recess 23' and further a second recess 24' which is positioned referring to FIG. 27 above the recess 23' in the conical portion of the female end piece 2'. The male portion of the female/male connector piece 4'''''' according to a seventh embodiment comprises a projection 432'''''' which is attached to the middle portion 43''''''. The projection 432'''''' which extends over the whole width of the middle portion 43'''''' is adapted to match with the second recess 48'''''' of another female/male connector piece 4''''''. This provides additional preliminary fixation when the bone screw or the locking cap is not yet inserted and may create a more stable construct once the screw and/or cap is locked.

Figure 30A:
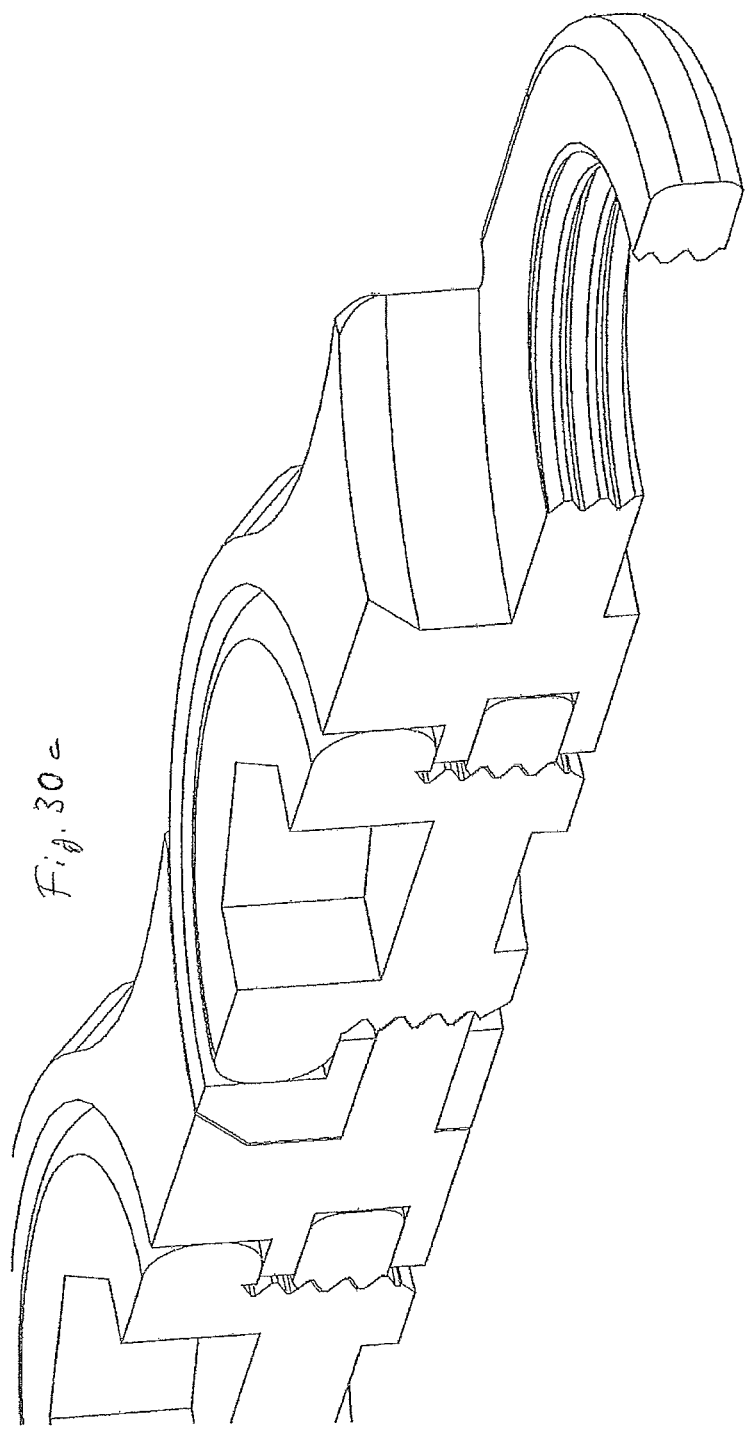
FIG. 30a shows a perspective view of a modular bone plate according to an eleventh embodiment.
Figure 31C:
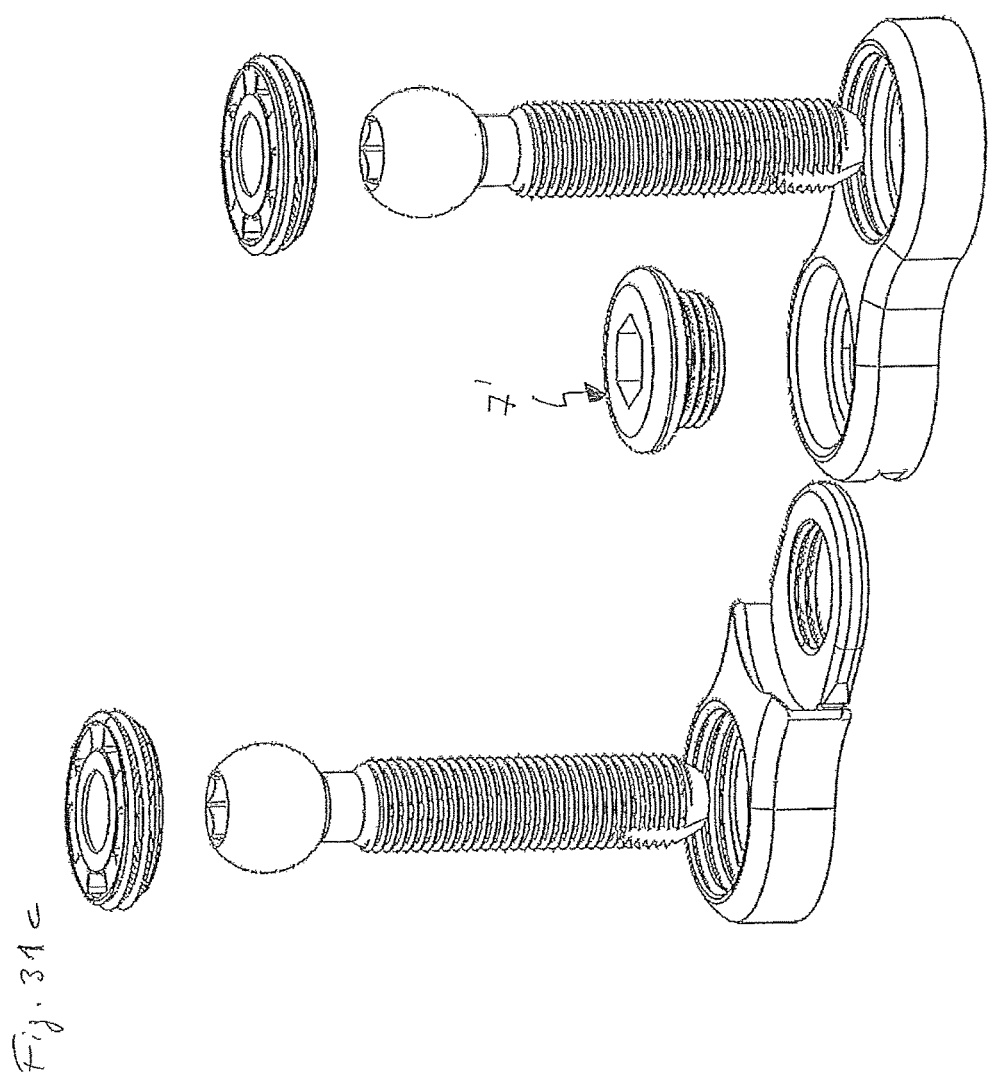
FIG. 31c shows an exploded view of the modular bone plate assembly according to the eleventh embodiment.

An eleventh embodiment of the modular bone plate 10'''' and the modular bone plate 100 will be described with reference to FIGS. 30 to 31. The difference referring to the above-mentioned embodiments is that the male portion comprises an internal thread 101'''' in the hole and the female portion of the female/male connector piece is threadless. The connection can be fixed with an ordinary screw 7'. The plate is also suitable for being used with ordinary bone screws without ball-shaped head.

The connector piece may also be a longer piece with one or several additional holes and a female and a male portion at the ends.

Figure 32A:
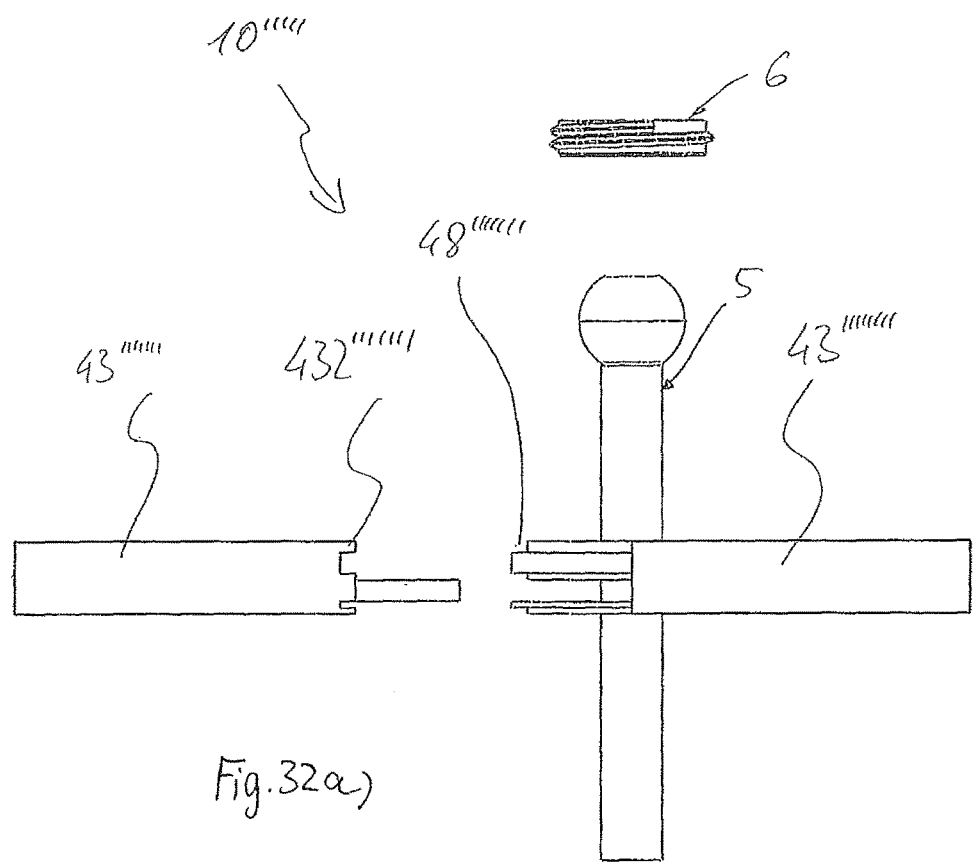
FIG. 32a shows a side view of a modular bone plate assembly according to the twelfth embodiment.
Figure 32B:
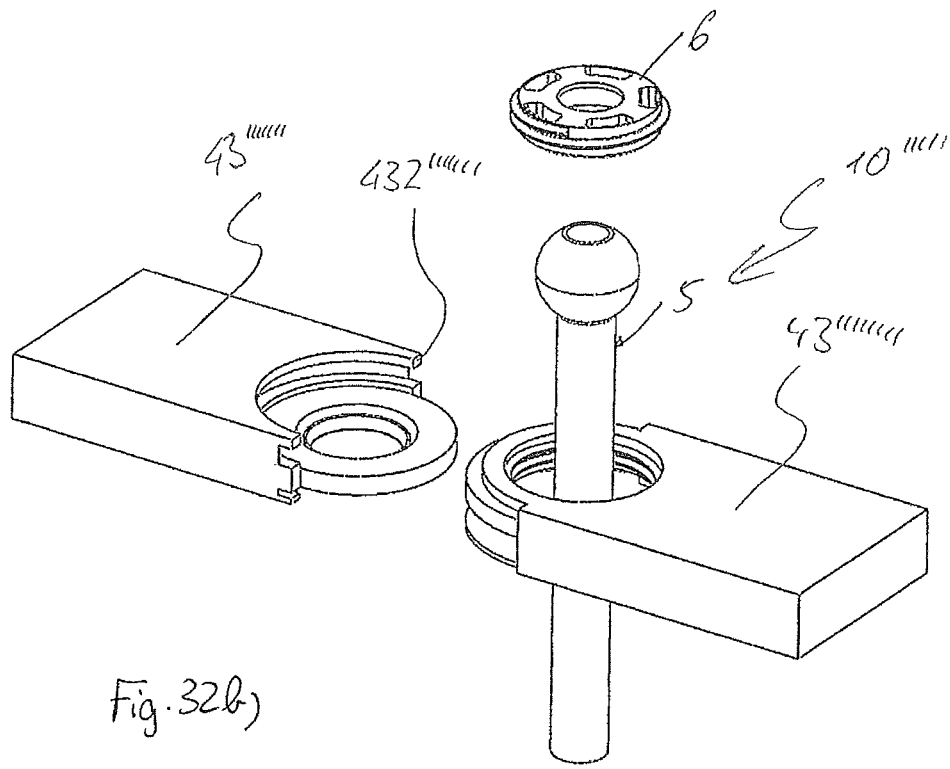
FIG. 32b shows an exploded view of the modular bone plate assembly according to the twelfth embodiment.
Figure 32C:
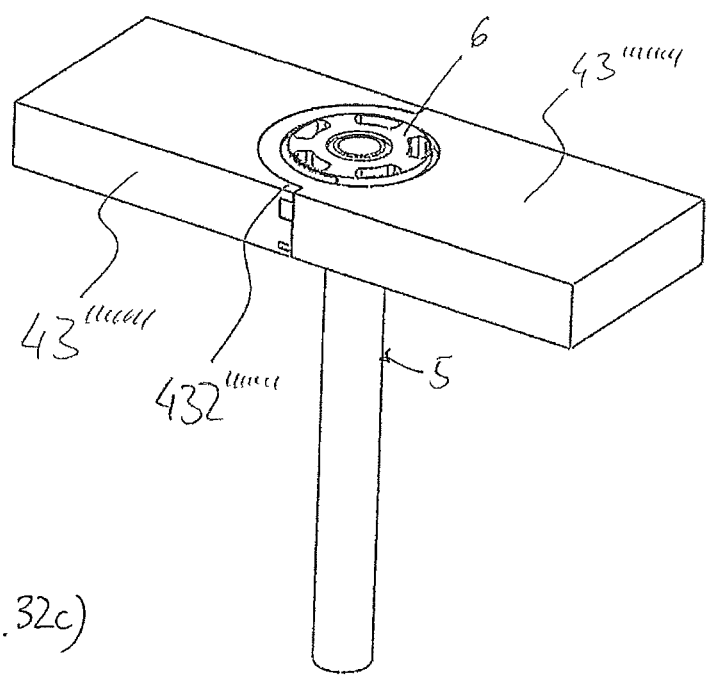
FIG. 32c shows a perspective view of the modular bone plate assembly according to the twelfth embodiment.

A twelfth embodiment of the modular bone plate 10'''' will be described with reference to FIGS. 32*a* to 32*c*. The difference to the tenth embodiment is that the projection 432'''''' is attached at the middle portion 43'''''' of a first member such that an upper face of the projection 432'''''' is flush with an upper face of the middle portion 43''''''. The second recess 48'''''' is attached to a middle portion 43'''''' of a second member such that it matches with the projection 432''''''. This provides the same advantages as the tenth embodiment and facilitates manufacturing. Further, a second projection may be attached to the middle portion of the first member such that a lower face of the projection is flush with a lower face of the middle portion. The corresponding third recess is provided at the second member.

The features of the embodiments can be combined among each other.

The parts of the bone plate are made of biocompatible materials such as biocompatible metal or metal alloys such as titanium, stainless steel, Ni—Ti alloys, for example Nitinol, or biocompatible plastic materials, such as PEEK (polyetheretherketone). The parts may all be of the same material or of different materials.

The invention claimed is:

1. A modular bone plate comprising:
   a first member comprising a top surface, a bottom surface, and a male connection portion with a single hole extending from the top surface to the bottom surface; and
   a second member comprising a top surface, a bottom surface, and a female connection portion having a side wall extending between the top and bottom surfaces, the side wall having an inner surface an outer surface, and a recess that extends through the side wall from the outer surface to the inner surface and that separates at least part of the female connection portion into an upper region and a lower region, and the second member further having a single hole extending from the top surface to the bottom surface and through both the upper region and the lower region,
   wherein when the male connection portion is inserted into the recess of the female connection portion to connect the first and second members, the holes of the male and female connection portions are configured to overlap with one another such that an anchor or a plug member is insertable into the overlapping holes, while the first and second members are pivotable relative to one another around a central axis of the overlapping holes.

2. The modular bone prate of claim 1, wherein the holes are closed in a circumferential direction.

3. The modular bone plate of claim 1, wherein the hole of at least one of the female connection portion or the male connection portion is threaded.

4. The modular bone plate of claim 3, further comprising:
the anchor comprising a head with a spherical segment and
a cap to be screwed into the hole that is threaded.

5. The modular bone plate of claim 3, further comprising the plug member configured to be connected to the hole of the female connection portion.

6. The modular bone plate of claim 5, wherein the hole of the female connection portion is threaded, and wherein the plug member is configured to be screwed into the threaded hole of the female connection portion.

7. The modular bone plate of claim 1, wherein the first member and the second member are configured to be fixed relative to one another at an angle.

8. The modular bone plate of claim 1, wherein the recess of the female connection portion communicates with the hole of the female connection portion.

9. The modular bone plate of claim 1, wherein the male connection portion is formed by a tongue portion or a projection portion.

10. The modular bone plate according to claim 1, wherein the female connection portion is substantially cylindrical, and wherein the recess extends circumferentially around about half of the side wall of the female connection portion.

11. The modular bone plate according to claim 1, wherein the male connection portion is cylindrical and has an extension to one side of the cylinder that is adapted to a contour of the side wall that defines the recess of the female connection portion.

12. The modular bone plate according to claim 1, wherein the recess defined by the female connection portion of the second member has a circular portion and two straight portions forming an angled configuration in a plane parallel to a top or bottom surface of the modular bone plate.

13. A modular bone plate comprising:
a first member comprising a top surface, a bottom surface, and a male connection portion with a single hole extending from the top surface to the bottom surface; and a second member comprising a top surface, a bottom surface, and a female connection portion having a side wall extending between the top and bottom surfaces, a recess that extends through the side wall and that separates at least part of the female connection portion into an upper region and a lower region, and a single hole extending from the top surface to the bottom surface and through both the upper region and the lower region, wherein when the male connection portion is inserted into the recess of the female connection portion to connect the first and second members, the holes of the male and female connection portions are configured to overlap with one another such that an anchor or a plug member is insertable into the overlapping holes, while the first and second members are pivotable relative to one another around a central axis of the overlapping holes, and wherein the second member extends along a longitudinal axis perpendicular to the central axis of the overlapping holes, and wherein the male connection portion is insertable along the longitudinal axis into the recess of the female connection portion.

* * * * *